(12) United States Patent  (10) Patent No.: US 7,922,670 B2
Jones et al.  (45) Date of Patent: Apr. 12, 2011

(54) SYSTEM AND METHOD FOR QUANTIFYING AND MAPPING VISUAL SALIENCE

(76) Inventors: Warren Jones, New Haven, CT (US); Ami Klin, Guilford, CT (US)

(*) Notice: Subject to any disclaimer, the term of this patent is extended or adjusted under 35 U.S.C. 154(b) by 542 days.

(21) Appl. No.: 11/360,787

(22) Filed: Feb. 23, 2006

(65) Prior Publication Data
US 2006/0189886 A1 Aug. 24, 2006

Related U.S. Application Data

(60) Provisional application No. 60/656,484, filed on Feb. 24, 2005.

(51) Int. Cl.
*A61B 13/00* (2006.01)
*A61B 3/14* (2006.01)
(52) U.S. Cl. ........................ 600/558; 351/209
(58) Field of Classification Search .................. 600/558; 351/209
See application file for complete search history.

(56) References Cited

U.S. PATENT DOCUMENTS

| | | | | |
|---|---|---|---|---|
| 5,035,500 | A * | 7/1991 | Rorabaugh et al. | 351/226 |
| 5,880,812 | A * | 3/1999 | Solomon | 351/210 |
| 6,102,870 | A | 8/2000 | Edwards | 600/558 |
| 6,601,021 | B2 * | 7/2003 | Card et al. | 702/187 |
| 6,670,963 | B2 | 12/2003 | Osberger | 345/629 |
| 6,712,468 | B1 | 3/2004 | Edwards | 351/209 |
| 6,755,527 | B1 | 6/2004 | Goldberg | 351/209 |
| 7,384,145 | B2 * | 6/2008 | Hetling et al. | 351/219 |
| 7,396,129 | B2 * | 7/2008 | Endrikhovski et al. | 351/209 |
| 2002/0154833 | A1 * | 10/2002 | Koch et al. | 382/325 |
| 2003/0158497 | A1 * | 8/2003 | Graham et al. | 600/558 |
| 2004/0015098 | A1 * | 1/2004 | Souvestre | 600/558 |

OTHER PUBLICATIONS

Alfred L. Yarbus, "Eye Movement and Vision", 1967, p. 171-211.
David S. Wooding, "Eye Movement of large population: II Deriving regions of interest, coverage, and similarity using fixation maps", Behavior Research Methods, Instruments, & Computers, 2002, p. 518-52811 pages.
Boris M. Velichkovsky et al., "New Technological Windows in Mind: There is More in Eyes and Brains for Human-Computer Interaction", CHI 96, 1996, p. 496-503.
Boris M. Velichkovsky et al., "Visual Fixations and Level of Attentional Processing", Eye Tracking Research & Applications Symposium, 2000, p. 79-85.
Michael Schiessel et al., "Eye tracking and its application in usability and media research", MMI-Interaktiv, Nr.6, Mar. 2003, p. 41-50.
Robert W. Reeder et al., "WebEyeMapper and WebLogger: Tools for Analyzing Eye Tracking Data Collected in Web-use Studies", 2000, 2 pages.
Simon Lessing et al., "IICap—A New Environment for Eye Tracking Data Analysis", 2002, 48 pages.

* cited by examiner

*Primary Examiner* — Max Hindenburg
*Assistant Examiner* — H. Q. Nguyen
(74) *Attorney, Agent, or Firm* — St. Onge Steward Johnston & Reens LLC

(57) ABSTRACT

A system for quantifying and mapping visual salience to a visual stimulus, including a processor, software for receiving data indicative of a group of individual's ocular responses to a visual stimulus, software for determining a distribution of visual resources at each of at least two times for each of at least a portion of the individuals. The system further including software for determining and quantifying a group distribution of visual resources at each of the at least two times and software for generating a display of the group's distribution of visual resources to the visual stimulus.

34 Claims, 17 Drawing Sheets

US 7,922,670 B2

SYSTEM AND METHOD FOR QUANTIFYING AND MAPPING VISUAL SALIENCE

CROSS-REFERENCE TO RELATED APPLICATIONS

This application claims priority benefits under 35 §U.S.C. 119(e) of the U.S. Provisional Application No. 60/656,484, filed on Feb. 24, 2005, herein incorporated by reference.

FIELD OF THE INVENTION

The invention relates to eye tracking, and more specifically to a system and method for the quantifying and mapping of visual salience to static or dynamic visual stimuli.

BACKGROUND OF THE INVENTION

Devices exist to measure and record eye movements. While many variations exist, eye tracking devices often include a camera attached to a computer which focuses on one or both of an individual's eyes and records eye movement. Some of such devices use contrast to locate the center of the pupil and use infrared illumination to create one or more corneal reflections, and relating the position of these points to determine a fixation point of the eye.

Eye movement data is typically categorized as fixations, smooth pursuit movements, saccades, or blinks. A fixation is said to occur when the eye gaze pauses in a certain position while a saccade is when one's gaze is moving to another position. By measuring and recording these movements, eye tracking devices may be used to determine where on a two-dimensional plane or image a viewer is looking and for how long. Further, the path one's eyes followed over the image may also be determined.

Eye tracking devices have many applications including, for example, advertising and market research. As disclosed in U.S. Pat. No. 6,712,468, eye tracking devices have been used to track the eyes of a person viewing a webpage. Representations may then be generated to show, e.g., designers of the webpage which regions of the webpage were viewed and which regions were not.

SUMMARY OF THE INVENTION

It is an object of the present invention to provide a system and method for quantifying and mapping visual salience of visual stimuli.

It is a further object of the present invention to provide a system and method for representing and quantifying the distribution of visual resources of groups of individuals in response to a visual stimulus. It is also an object to provide a system and method for comparing individuals or groups of individuals to a target group. It is also an object to provide a system and method for representing and quantifying the distribution of visual resources of groups of individuals to a dynamic visual stimulus to identify locations and times of heightened attention to the visual sitmulus.

Still another object of the present invention is to provide a system and method for comparing and quantifying the ocular responses and distribution of visual resources to visual stimuli of individuals or groups of individuals.

These and other objectives are achieved by providing a system for quantifying and mapping visual salience to a dynamic visual stimulus, including a processor, software executing on the processor for receiving data indicative of a group of individual's ocular responses to a dynamic visual stimulus, software executing on the processor for determining a distribution of visual resources at each of at least two times for each of at least a portion of the individuals, software executing on the processor for determining a group distribution of visual resources at each of the at least two times, and software executing on the processor for generating a display of the group's distribution of visual resources to the dynamic visual stimulus.

In some embodiments, the software for determining a distribution of visual resources of the system determines each distribution based on the data and a distribution of biological resources such as retinal cells, cortical magnification, or other. Also in some embodiments, the display of the group's distribution of visual resources includes an area of maximal salience at each of the at least two times corresponding to areas of the visual stimulus, wherein the areas of maximal salience are extruded over time to represent an attentional funnel.

Further provided is a system for quantifying and mapping visual salience to a static visual stimulus, including a processor, software executing on the processor for receiving data indicative of a group of individual's ocular responses to a static visual stimulus, software executing on the processor for determining a distribution of visual resources at each of at least two times for each of at least a portion of the individuals, software executing on said processor for determining a group distribution of visual resources at each of the at least two times, and software executing on the processor for generating a three-dimensional display of the group's distribution of visual resources to the static visual stimulus over time.

Further provided is a method for quantifying and mapping visual salience to a visual stimulus, including the steps of receiving data indicative of a group of individual's ocular responses to a visual stimulus, determining a distribution of visual resources at each of at least two times and for each of at least a portion of the individuals of the group, determining a group distribution of visual resources at each of the at least two times, and generating a display of the group's distribution of visual resources to the visual stimulus over time.

In some embodiments, the method includes the steps of receiving subject data indicative of a subject's ocular responses to the visual stimulus, determining at least one point of regard at each of the at least two times based on the subject data, generating a display of the subject's at least one point of regard, and comparing a display of the subject's at least one point of regard to the display of the group's distribution of visual resources to the visual stimulus.

Other objects, features and advantages according to the present invention will become apparent from the following detailed description of certain illustrated embodiments when read in conjunction with the accompanying drawings in which the same components are identified by the same reference numerals.

DETAILED DESCRIPTION OF THE INVENTION

Figure 1:
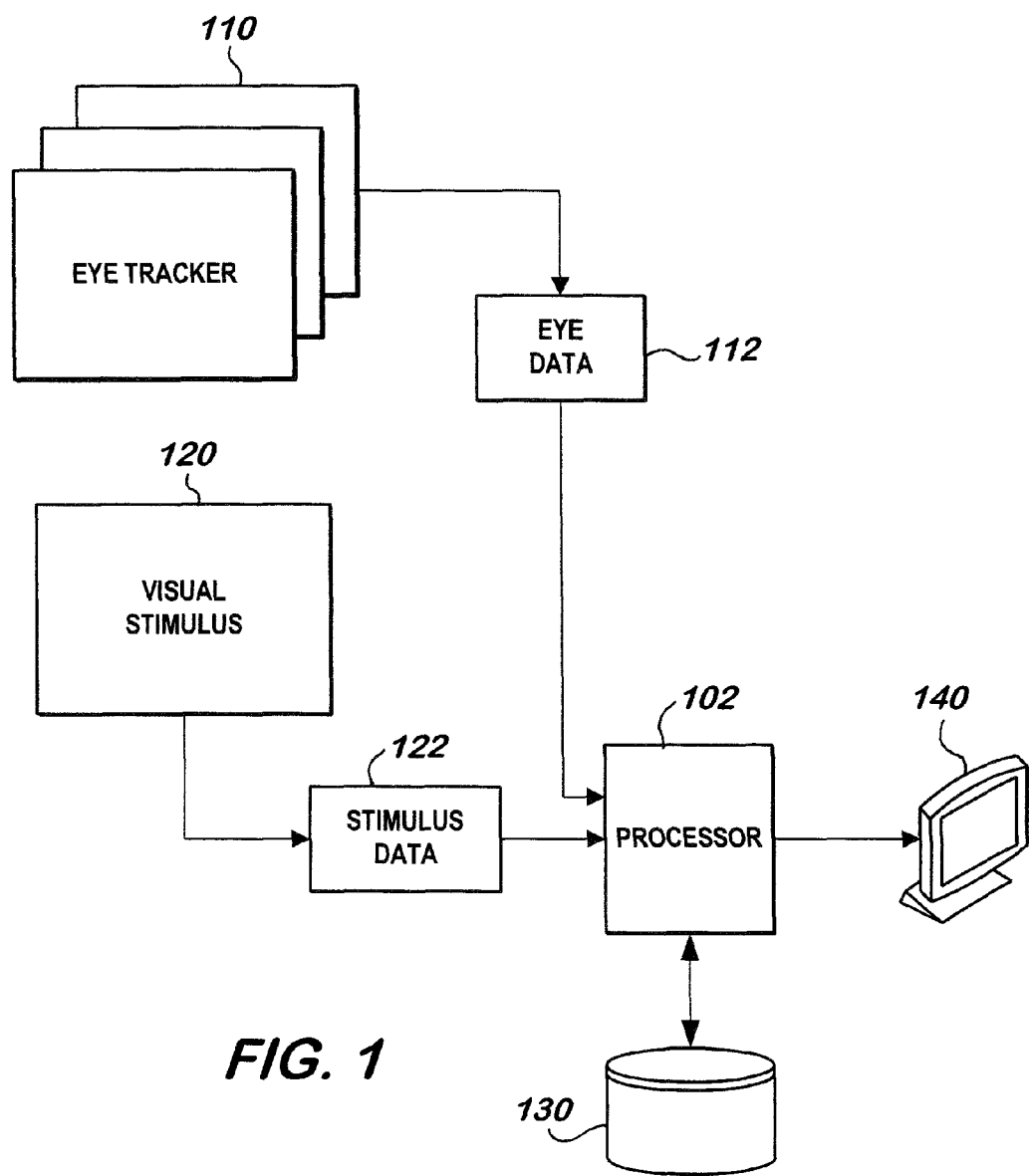
FIG. 1 is a system for quantifying and mapping visual salience.

FIG. 1 illustrates an exemplary system for quantifying and mapping visual salience. The system includes at least one processor 102. Processor 102 may be any type of device designed to receive and execute software programs, or that which is designed to be modified in functionality by software programs. For example, the processor 102 may be selected from a group consisting of digital signal processors, microcontrollers, and microprocessors, or a group consisting of field programmable gate arrays, and computer programmable logic devices. The functionality associated with the processor 102 may be centralized or distributed, whether locally or remotely.

The processor 102 includes software executing thereon for receiving data indicative of a group of individual's ocular responses to a visual stimulus, e.g., visual stimulus 120. For example, the processor 102 may receive eye data 112 from any number of eye trackers 110 or eye tracking devices. Each eye tracker 110 may be any device for tracking the movement of at least one eye of an individual (e.g., individual human or any other species/animal). For example, the eye tracker 110 may be an infrared video-oculography eye tracking device. In some embodiments, the eye tracker 110 is a binocular eye tracker. Each eye tracker 110 may generate eye data 112 indicative of ocular responses such as eye movements, direction, dilation, rotation and/or gaze.

Based on the eye data 112, the processor 102 may determine and/or identify points of regard. A point of regard is a point at which an eye and/or both eyes of an individual are focusing. A point of regard may be indicated as a coordinate in space (e.g., x, y, z) or a two-dimensional coordinate data (e.g., x, y) on a surface or visual stimulus portrayed on a surface. A point of regard may additionally be referenced with a time (t). Each point of regard may indicate a point of fixation or any point of at which an eye is focusing regardless of the length of time or fixation on the point.

In some embodiments, the system includes a visual stimulus 120. The visual stimulus 120 may be any visual stimulus such as a still image (e.g., print ad, webpage, painting, etc.), video imagery, or interactive media. In a preferred embodiment, the visual stimulus 120 is a dynamic visual stimulus such as a video. The video may include any imagery, broadcast, recording and/or representation of visual images of stationary or moving objects including, but not limited to, a motion picture, a video game, and/or a recording of a live event. The video may be embodied in any form of media such as film, video tape, DVD, CD-ROM and/or digital storage (e.g., storage 130). The visual stimulus 120 may also be a live event (e.g., theatrical performance, social interaction, training exercise, etc) or any representation thereof (either two- or three-dimensional).

Some embodiments of the system further include software for receiving stimulus data 122 from the visual stimulus 120. The stimulus data 122 may be, for example, data representing the visual stimulus 120 (e.g., representation or video recording of a live event), a complete video visual stimulus 120, or any portion of a visual stimulus 120 (e.g., frames and/or screenshots).

The system may also include a storage 130. The storage 130 may be collocated with the processor 102 or may be remotely located, e.g., and accessible via a communications network. The storage 130 may provide temporary storage for the processor 102 (e.g., random access memory) and/or permanent or semi-permanent data storage, e.g., for eye data 112 or stimulus data 122. The system may further include any number of displays 140. The display 140 may also be located either local or remote to the processor 102. For example, the display 140 may be remotely located and receive data or information from the processor 102 via the Internet. As will be described below, data representing points of regard, distributions of visual resources, and/or a group's distribution of visual resources and/or attention to the visual stimulus 120 may be presented on the display 140.

Figure 2:
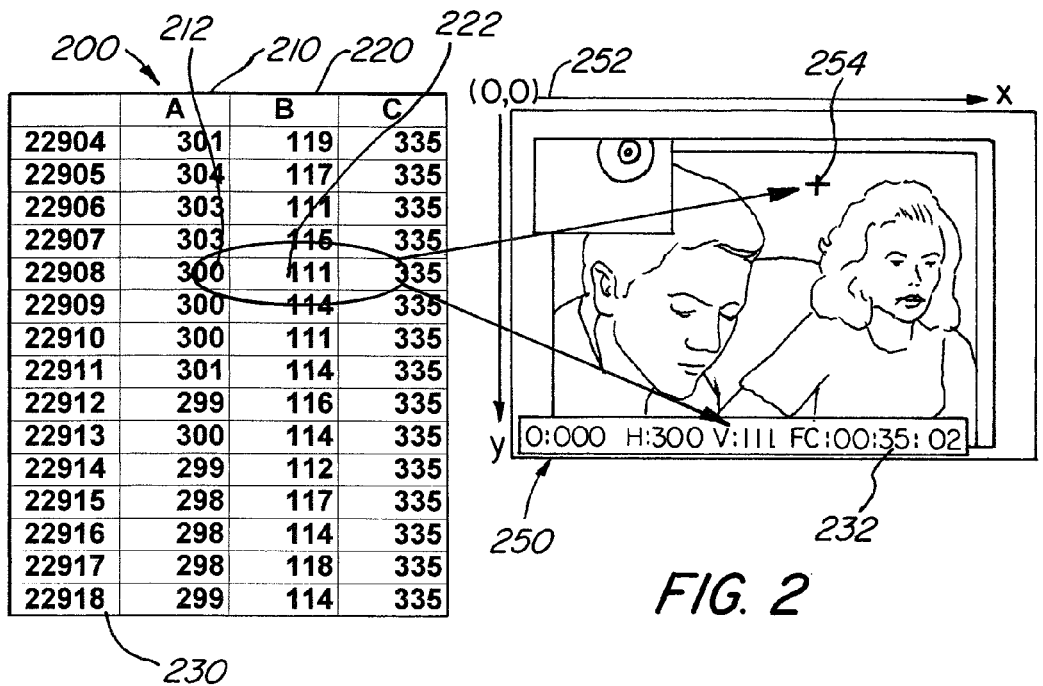
FIG. 2 is data indicative of ocular responses to a visual stimulus.

FIG. 2 shows an exemplary table 200 of data indicative of ocular responses to a visual stimulus, or eye data 112. It should be understood that the eye data 112 may be organized and/or maintained in any manner or format and that the table 200 is only exemplary. As such, the table 200 may be organized in any manner such as in columns 210, 220, 230 as shown. In the present illustration, the data is referenced as coordinates describing points of regard. For example, an x-value of 300 is shown at 212 with a corresponding y-value of 111 at 222. The coordinate in the present example further includes a time value in column 230, e.g., referring to a time that the particular coordinate of eye data 112 was sampled. The time value may further correspond to a time 232 of a visual stimulus 250. Any number of additional categories (e.g., columns) of eye data 112 may be represented such as a z-value referring to a distance for the point of regard.

As shown in FIG. 2, a point of regard in the table 200 may be mapped to the visual stimulus 250. For example, the point of regard referenced at 212 and 222 may be mapped to a point 254 on a portion of the visual stimulus, e.g., using a coordinate system 252. The coordinate system 252 may, in some embodiments, relate to any video pixel coordinate system (e.g., 640×480 or 720×480). The portion of the visual stimulus 250 may be a portion (e.g., frame or panel) corresponding to the time at which the point of regard was sampled.

The eye data 112 may include data sampled at any rate or frequency. For example, eye data 112 may be sampled from an individual at a sampling frequency of 60 Hz, 512 Hz, 1000 Hz, or any other sampling frequency. The rate of visualization or presentation of eye data may be increased or decreased as desired and/or adjusted based on a rate of change of the dynamic visual stimulus, e.g., 250. Both rates of analysis and rates of presentation of eye data may also be based on analysis of meaningful segments of video isolated for scrutiny. For example, if meaningful events in the stimuli occur at a rate of 30 times per second, rates of sampling, analysis, and presentation could equal or exceed 30 Hz.

Figure 3:
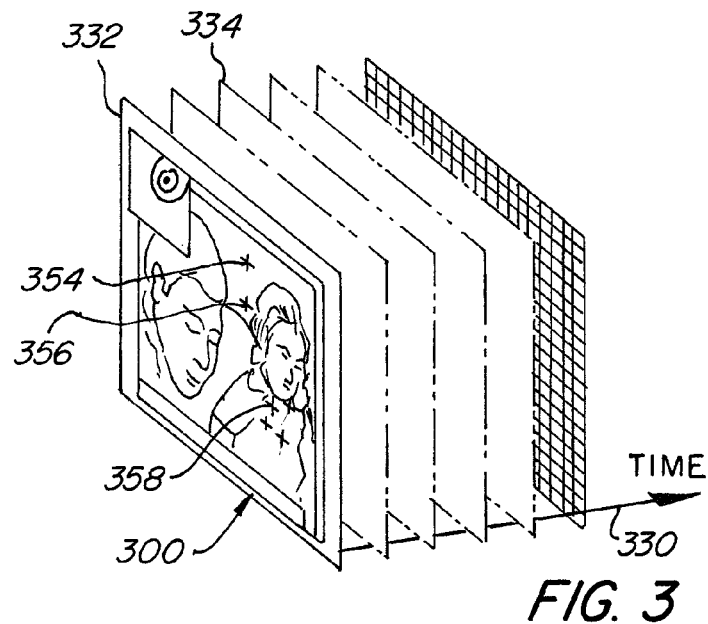
FIG. 3 is a display of portions of a dynamic visual stimulus over time and data indicative of ocular responses to the dynamic visual stimulus.

FIG. 3 shows a display 300 of several portions and/or frames of a dynamic visual stimulus. As shown, the display 300 includes a time axis 330 and any number of frames, e.g., 332, 334, corresponding to different times of the dynamic visual stimulus. Further represented in the display 300 are points of regard, e.g., 354, 356, 358, on the frame 332. Each of the points of regard may be determined from eye data 112 sampled from different individuals. Alternatively, each point of regard may be determined from different viewings of the same dynamic visual stimulus by one individual.

Figure 4:
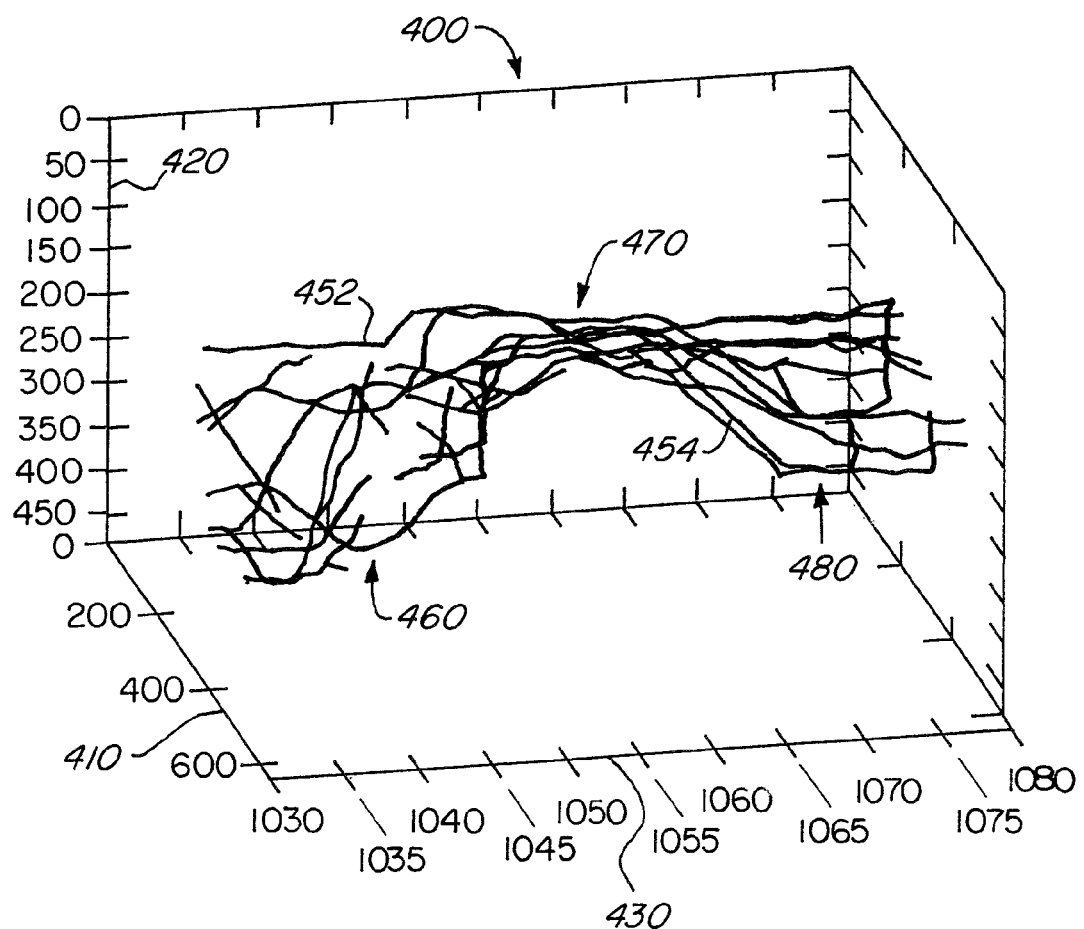
FIG. 4 is display of points of regard over time.

FIG. 4 shows a display 400 of points of regard over time. The display 400 includes a coordinate system having an x-axis 410, y-axis 420, and a time axis 430. The system of the present invention includes software for generating a display of the at least one individual's response and/or distribution of visual resources to the visual stimulus. In the present example, a scanpath for each of a group of individuals is displayed as individual points of regard over time. For example, the display 400 includes any number of representations or scanpaths, e.g., 452, 454, each pertaining to one individual's ocular responses to a dynamic or static visual stimulus over time. Alternatively, each scanpath may represent ocular responses experienced by the same individual upon multiple viewings of the same visual stimulus.

As shown, the present embodiment provides a unique means to present ocular response data of multiple individuals over time. By comparing each of the scanpaths shown in FIG. 4, any number of divergences 460, 480 and convergences 470 of visual salience may be identified. A divergence represents a time in which viewer's visual resources are not highly overlapping, e.g., when viewers watching the same visual stimulus are generally looking at different points or areas. A convergence represents a heightened attention to a corresponding area of the visual stimulus, i.e., where viewers' visual resources are highly overlapping. The display 400 may be a static display, e.g., depicting a distinct period or range of time, or a dynamic display. For example, the display 400 may be a continuous display changing over time. In either format, individuals' points of regard, the duration of divergences and convergences, and their orders over time, are advantageously presented in a single display 400. In some embodiments, portions (e.g., frames) of the visual stimulus may be mapped to the data and included in the display 400.

In one embodiment, an average point of regard may be determined by calculating an average or mean of all points of regard at that time. A mean deviation from that point may also be determined and used to define a radius about the mean point of regard. A defined area may be displayed to indicate a mean area of regard or fixation at the particular time (not shown). Such areas calculated for each of a number of times may further be extruded and/or connected to generate a three-dimensional representation of divergences and convergences in the visual stimulus over time. However, as will be described below, the present invention includes a further embodiment which takes into consideration biological factors, such as the distribution of retinal cells in the eye.

Figure 5A:
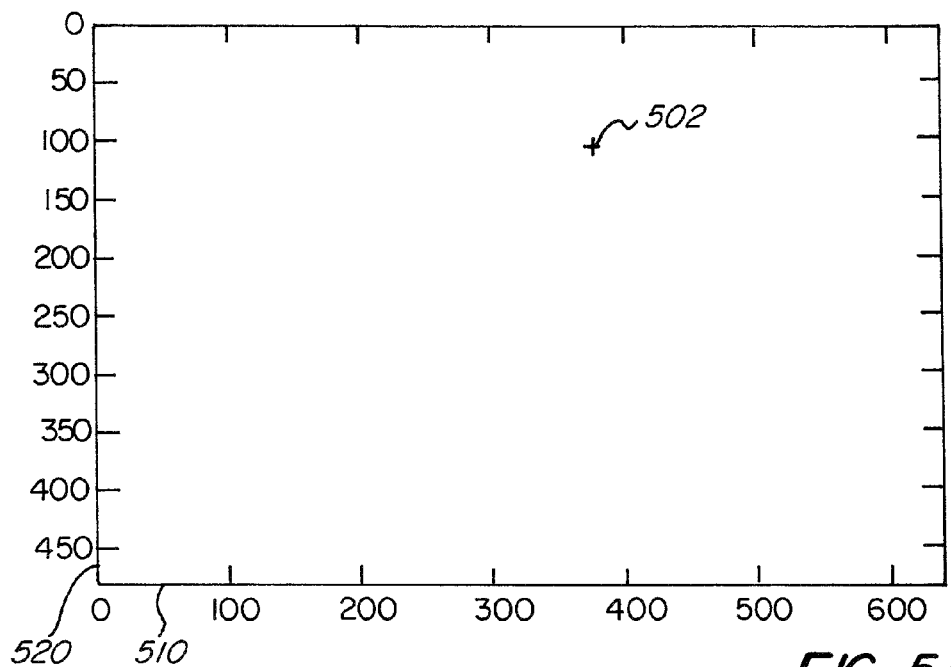
FIG. 5A is a coordinate display of data representing a point of regard.

Shown in FIG. 5A, a point of regard 502 may be displayed in a two-dimensional coordinate system. Each coordinate may correspond to a location on a portion of a visual stimulus. With respect to a dynamic visual stimulus, each coordinate may refer to a location on the stimulus as it appears at a particular time. While a point of regard 502 may indicate a point where an eye(s) is focused, such representation does not take into account that an individual's visual attention may be allocated according to a non-uniform distribution about each point of regard. The system therefore includes software for determining a distribution of visual resources (e.g., visual attention) based on a non-uniform distribution.

Figure 5B:
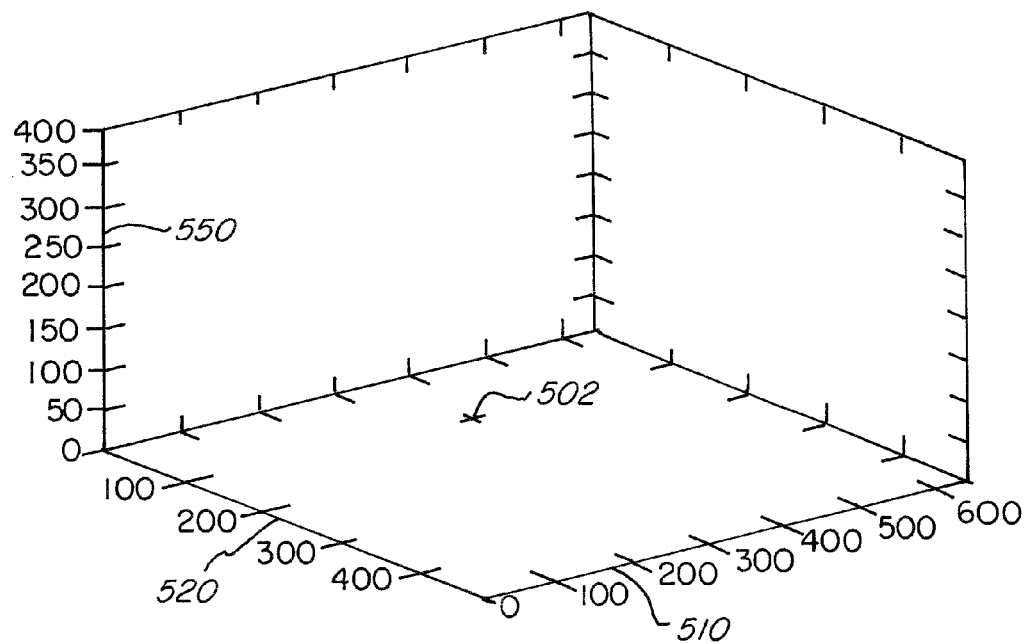
FIG. 5B is another coordinate display of data representing the point of regard shown in FIG. 5A.

FIG. 5B shows another display of the point of regard 502 for which a distribution of visual resources may be determined. The point of regard 502 is shown with reference to an x-axis 510 and y-axis 520. Further included in the display is a z-axis representing a value of relative salience. A distribution of one's visual resources directed at or around a particular point of regard may be determined by several different means. One such means is to use an index of biological resources in the eye, such as an index of retinal cell (e.g., ganglion cell) distribution in the eye. Preferably, the effective (e.g., sampling) distribution of retinal cells is used rather than the actual, anatomical distribution of retinal cells for increased accuracy. Some embodiments of the present therefore include software for determining and/or receiving data representing an effective distribution of retinal cells (e.g., ganglion cells) in an eye (or an approximation thereof). In some other embodiments, other distribution functions are used such as a distribution of cortical magnification factor, rod photoreceptors or a combinatorial distribution.

In one embodiment, a calculation of effective distribution of retinal ganglion cells is accomplished by first creating a density matrix describing the anatomical distribution of retinal ganglion cells (not shown). Next, a density matrix of the anatomical distribution of cone photoreceptors is created. A ratio of ganglion cells to cone photoreceptors across the entire retina is determined. The distribution of cone photoreceptors is then multiplied by the ratio to yield a map of effective retinal ganglion cells (not shown). Based on the viewer's field-of-view (e.g., field-of-interest, distance away from a plane of fixation), the retinal field-of-view may be subdivided to include only a portion of interest. A density of visual resources (e.g., density of cells) relative to the pixels or unit of viewing angle or unit of interest is thus determined. The distribution may then be doubled to provide a distribution for both eyes of a given individual.

Figure 5C:
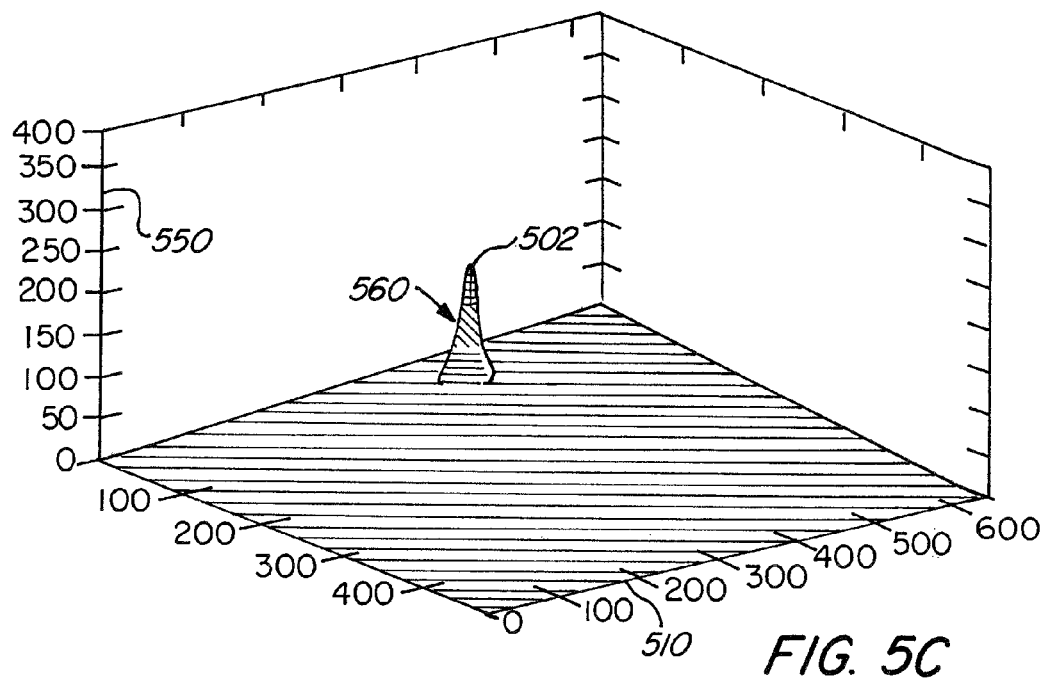
FIG. 5C is a topographical display of the point of regard shown in FIGS. 5A and 5B and an exemplary distribution of visual resources.
Figure 5D:
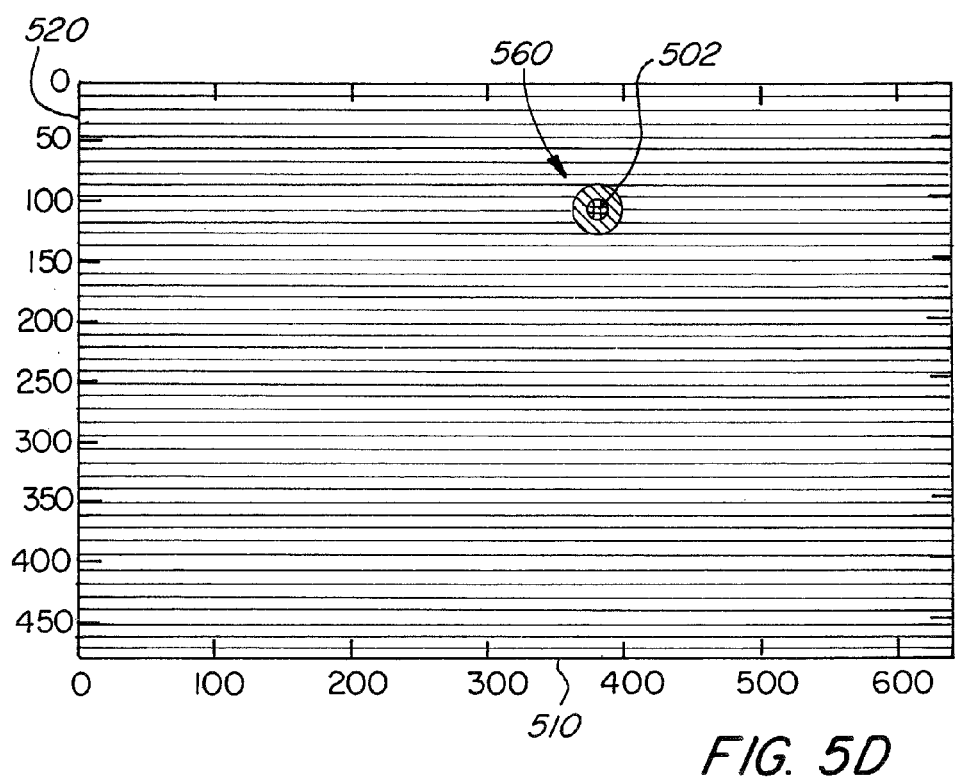
FIG. 5D is a two-dimensional display of the point of regard and distribution of visual resources shown in FIG. 5C.

Using the distribution of retinal cells and a point of regard 502, a distribution of visual resources 560 centered about the point of regard 502 may be generated and displayed topographically as shown in FIG. 5C. As shown in FIG. 5D, the distribution of visual resources 560 may also be shown two-dimensionally wherein the distribution is represented by a color gradient or pseudo-color mapping. In some embodiments, the distribution is shown as an overlay to the visual stimulus wherein a grayscale from black to transparent represents relative salience (not shown).

For any given time, any number of individual distributions of visual resources (e.g., 560) may be determined. For example, a distribution of visual resources may be determined for each point of regard from the eye data 112 at any number of particular times (e.g., each pertaining to a different individual's ocular response at the given time). Each distribution of visual resources may pertain to a different individual viewing the same visual stimulus, or each may pertain to the same individual upon different viewings of the same visual stimulus.

Figure 6A:
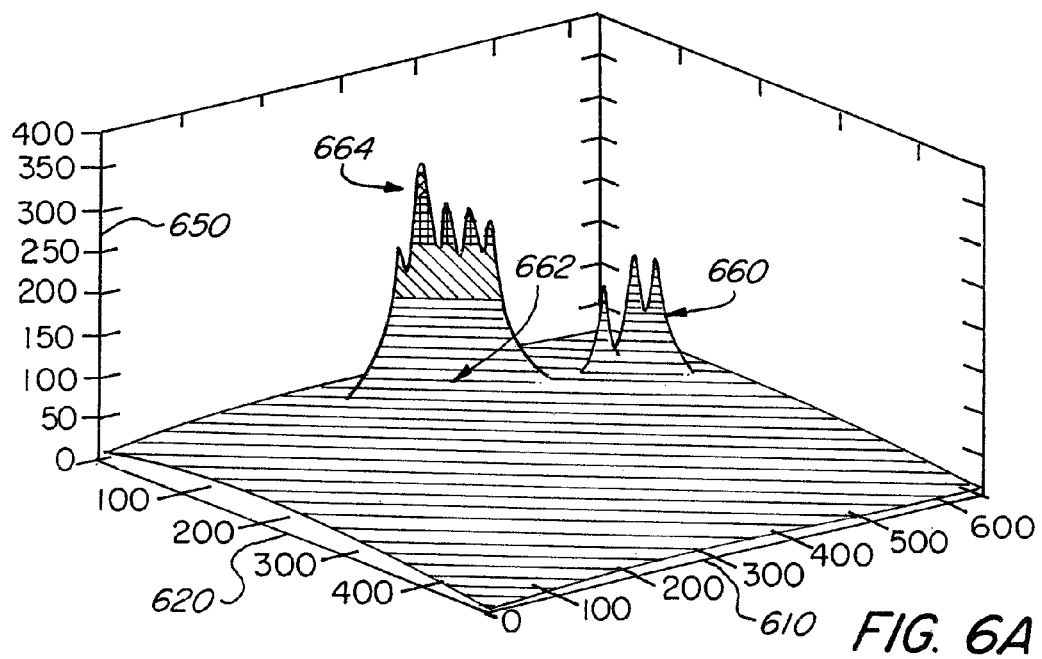
FIG. 6A is a topographical display of a group distribution of visual resources.

The system according to the present invention further includes software for determining a group distribution of visual resources at particular times. As shown in FIG. 6A, a group distribution of visual resources may be determined and represented by aggregating any number of individual distributions of visual resources (e.g., 660, 662, 664). Any means of aggregating the distributions may be used. For example, the distribution functions may be summed linearly to determine the group distribution. Alternatively, the distribution functions may be multiplied. Based on the group distribution of visual resources, an average (e.g., mean or median) value of relative salience 652 may be determined. A cross-section of the group distribution of visual resources may be taken at the average value 652 to determine an area or region of maximal salience at the particular time. The area of maximal salience at each particular time according to the present embodiment is therefore determined by the viewers and their distributions of visual resources, rather than by an approximation based on the locations or relative distances of points of fixation.

Figure 6B:
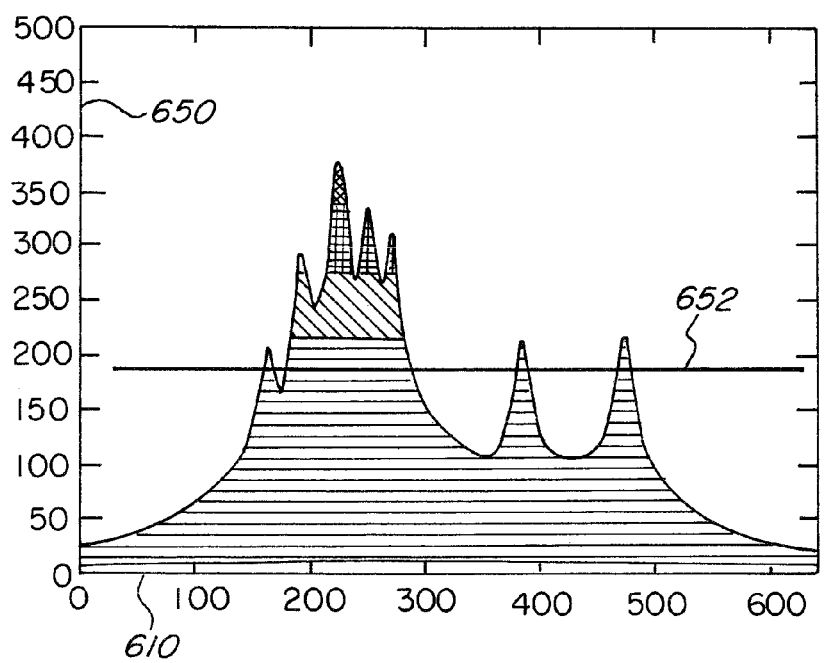
FIG. 6B is another display of the group distribution of visual resources shown in FIG. 6A.

A group distribution of visual resources, as shown in FIGS. 6A and 6B, may be determined or generated for any time, e.g., corresponding to a time of the dynamic visual stimulus. For example, a group distribution of visual resources may be generated at each sample time (e.g., according to sample rate of eye data). Alternatively, select times may be used, such as times corresponding to times or frames of interest in the visual stimulus.

Figure 7:
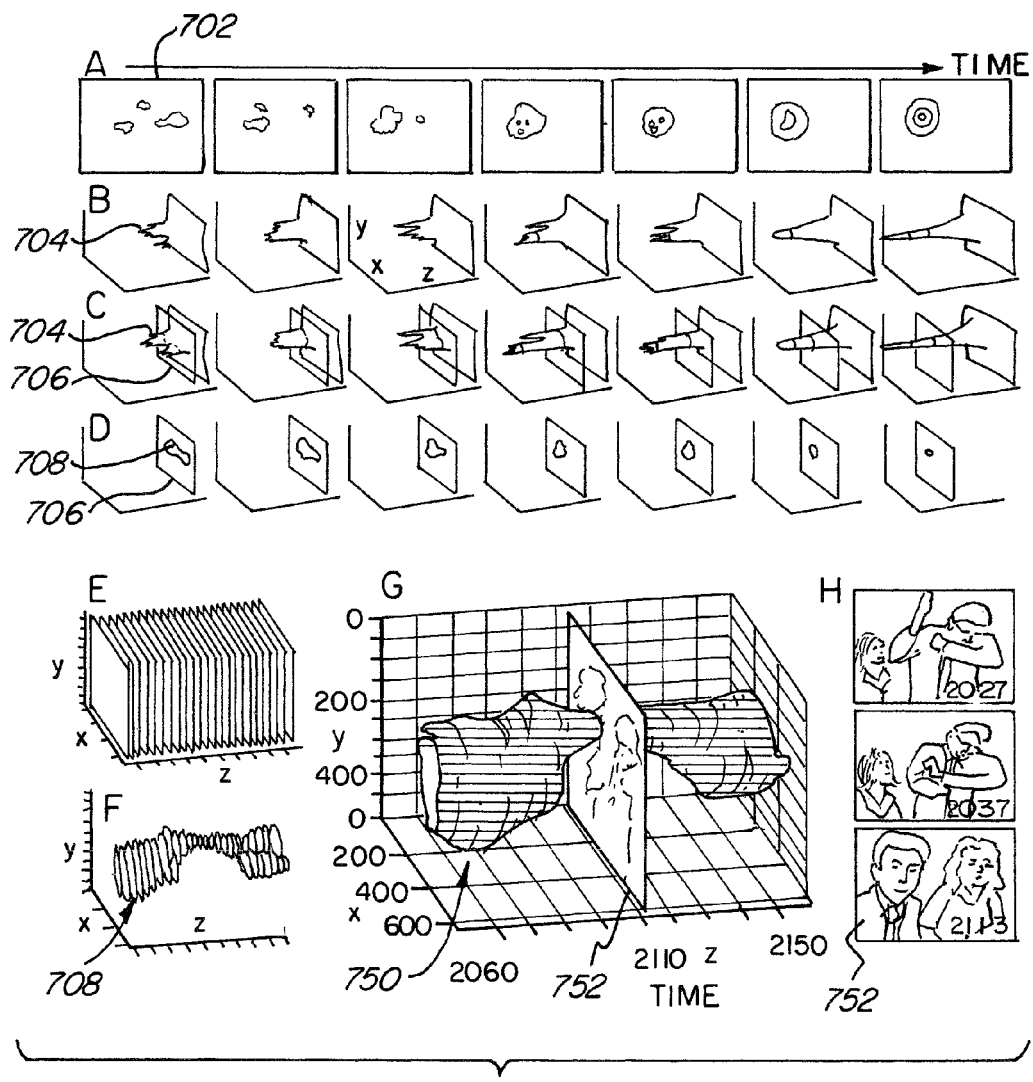
FIGS. 7A-7H show an exemplary generation of display of a group's distribution of visual resources.

The system according to the present invention further includes software for generating a display of the group's distribution of visual resources to the visual stimulus. FIGS. 7A-7H show an example of a means by which to generate a display of the group's distribution of visual resources according to the present invention. FIG. 7A shows two-dimensional representations of a group of ten individuals' distribution of visual resources (e.g., 702) at particular times in response to a visual stimulus. In FIG. 7B, the distributions are displayed topographically (e.g., 704) over the same period of time. As will be apparent to one skilled in the art upon reading the present description, the group's distribution of visual resources is changing over the exemplary period of time (i.e., from left to right) from divergent to convergent (i.e., identifying an area of heightened attention). FIG. 7C shows the group's distribution of visual resources at each time and a plane (e.g., 706) at an average (e.g., mean or median) value of relative salience or height value.

FIG. 7D shows each plane (e.g. 706) and an area of maximal salience (e.g., 708) provided by the plane at each time. FIGS. 7E and 7F further show the areas of maximal salience (e.g., 708) at any number of times. To generate a preferred display of the group's distribution of visual resources according to the present invention, the areas may be connected and/or extruded to develop an attentional funnel 750 over the period of time as shown in FIG. 7G. The funnel 750 may be mapped to the visual stimulus and portions (e.g., frame 752) of the visual stimulus included in the display to show the areas of the visual stimulus which correspond to the areas of maximal salience. As shown, a convergence is shown at the frame 752 indicating an area of heightened attention to the eyes of the male actor. FIG. 7H shows the frame 752 as well as two preceding frames leading up to the convergence.

Figure 8A:
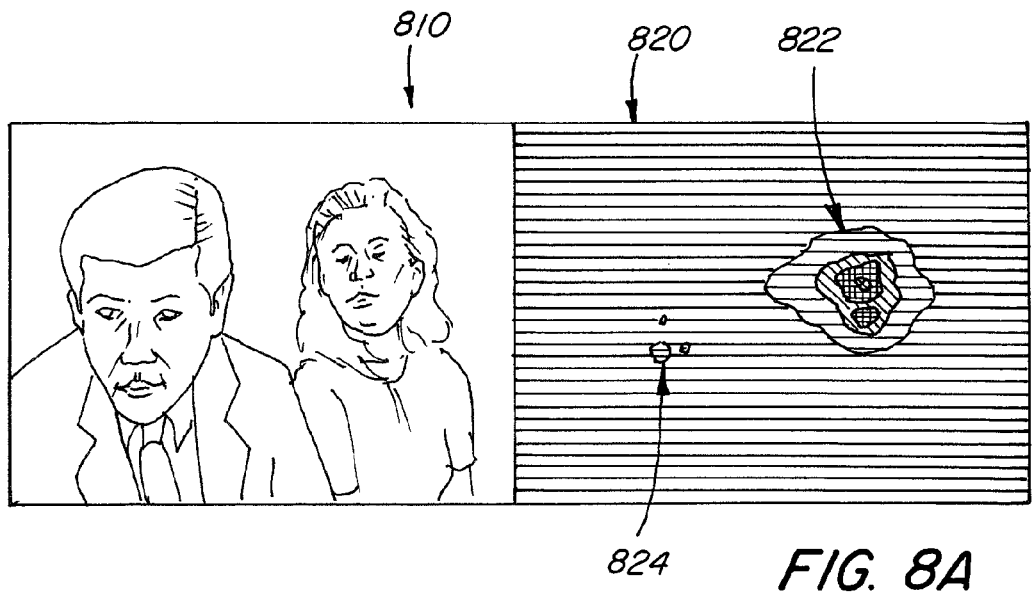
FIG. 8A is a screenshot of a display of a group's distribution of visual resources to a visual stimulus.
Figure 8B:
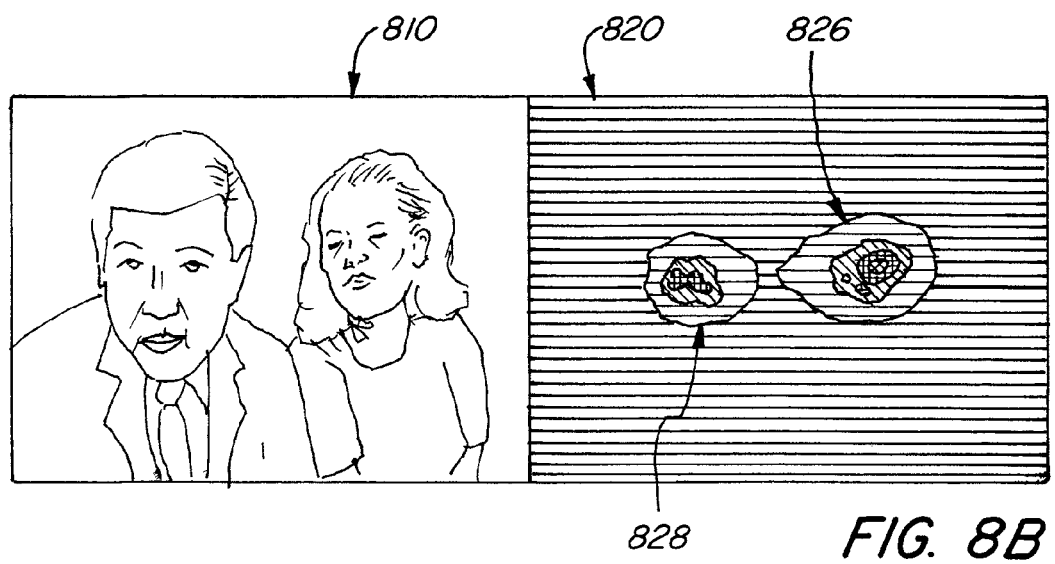
FIG. 8B is another screenshot of the display of a group's distribution of visual resources to the visual stimulus.

FIGS. 8A and 8B show two exemplary two-dimensional displays according to the present invention. As shown, a portion 810 of a visual stimulus may be displayed simultaneously with a display 820 of one or more areas of maximal salience, e.g., 822-828, determined as described above. The distribution of visual resources within the area may be represented by a color gradient or pseudo-color mapping. In some embodiments, the distribution is shown as an overlay to the visual stimulus wherein a grayscale from black to transparent represents relative salience (not shown). The display 820 may be static and depicting one particular time of the eye data sampling synchronized to the particular portion 710 (e.g., time and/or frame) of the visual stimulus. The display of the group's distribution of visual resources and/or attention may also be dynamic, e.g., showing the dynamic visual display and corresponding areas of maximal salience changing over time.

Figure 9A:
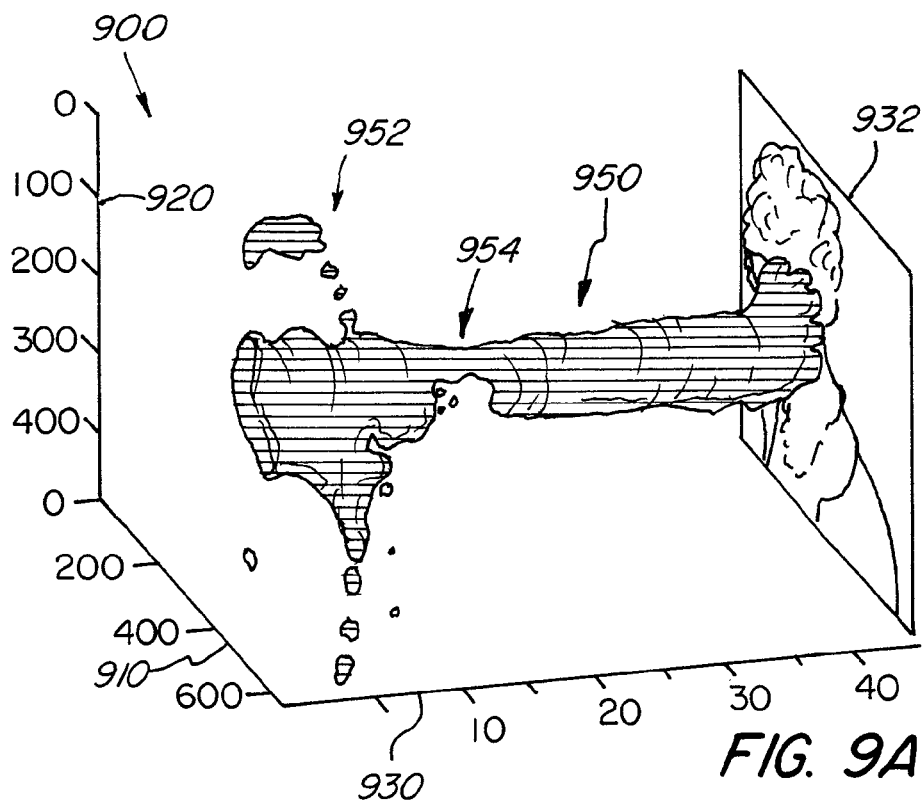
FIG. 9A is a screenshot of another display of a group's distribution of visual resources to a visual stimulus.
Figure 9B:
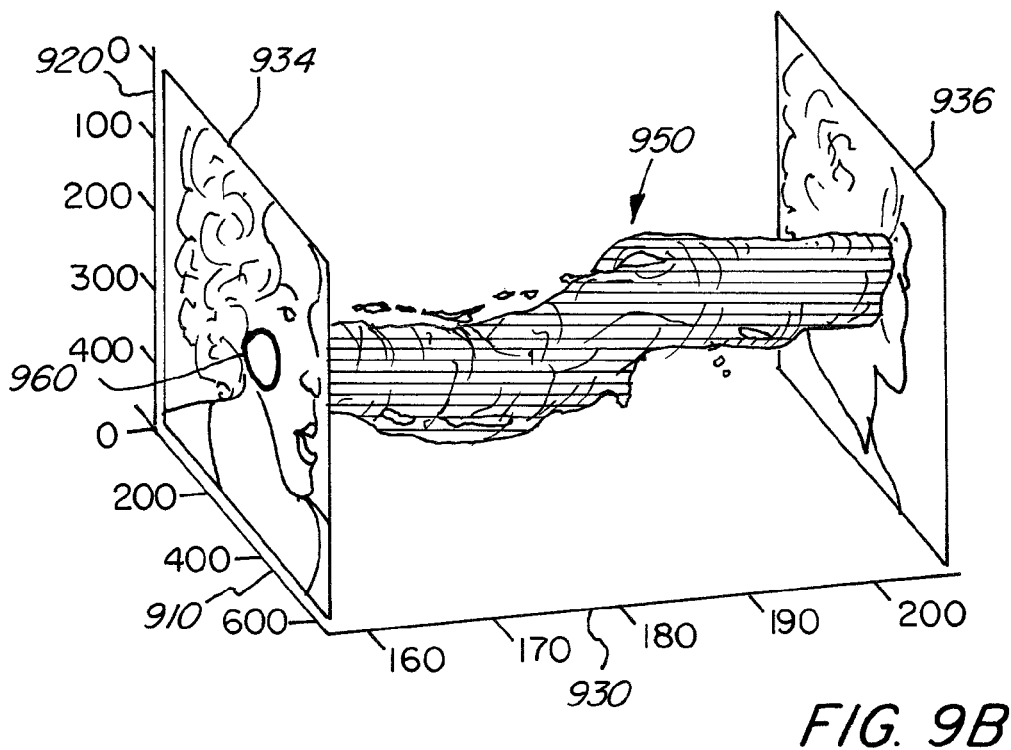
FIG. 9B is another screenshot of the display of the group's distribution of visual resources to the visual stimulus shown in FIG. 9A.
Figure 9C:
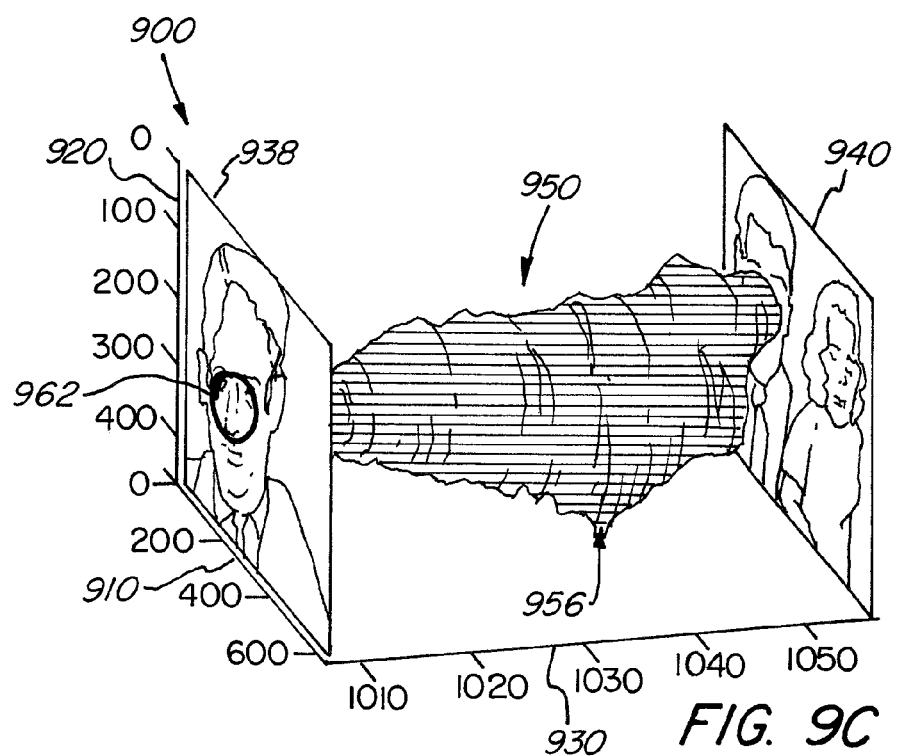
FIG. 9C is another screen shot of the display of the group's distribution of visual resources to the visual stimulus shown in FIGS. 9A and 9B.

FIGS. 9A-9C show screenshots of a preferable display 900 of a group's distribution of visual resources to a visual stimulus according to the present invention. Shown in FIG. 9A, the display 900 may include an x-axis 910, y-axis 920 and a time axis 930. The display 900 may be generated by connecting or extruding the areas of maximal salience over time to create an attentional funnel 950 as described with reference to FIGS. 7A-7H. The funnel 950 may be synchronized with corresponding times (e.g., frame 932) of a dynamic visual stimulus. For static stimuli, any number of representations of the visual stimulus may similarly be included in the display to depict the corresponding areas of maximal salience and/or heightened attention over time. The display 900 is also preferably a dynamic and/or streaming display. For example, the display 900 may include an attentional funnel 950 streaming through all or a portion of a dynamic visual stimulus (e.g., video). Likewise, the display 900 may include an attentional funnel 950 streaming through any number of representations (e.g., duplicate representations) of a static visual stimulus (e.g., print ad, painting, etc) over a period of time.

As shown in FIG. 9A, divergences (e.g., 952) of the group's visual resources, indicated by a widening of the funnel 950, and convergences (e.g., 954) of visual resources, indicated by a narrowing of the funnel 950, are readily apparent from the attentional funnel 950. Therefore, regions of interest and/or areas of heightened visual salience and/or attention to the visual stimulus may be identified at the convergences. As will be apparent to those of skill in the art, the present invention therefore provides a means to determine distinct instances of attention to a particular location at a particular time by a group of people, i.e., as revealed through the convergence of the attentional funnel 950.

Figure 9D:
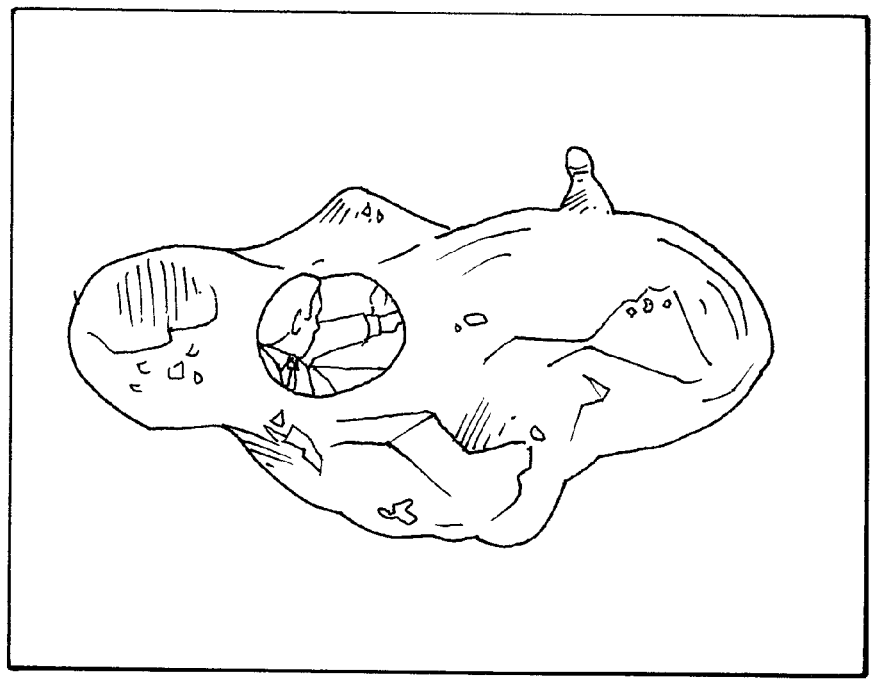
FIG. 9D is a screen shot of another display of a group's distribution of visual resources to the visual stimulus shown in FIGS. 9A-9C.

FIG. 9B shows another screenshot of the display 900 according to the present invention. In this particular figure, an area of maximal salience 960 is shown at a time 934 and represented as a cross-section of the attentional funnel 950. FIG. 9C shows another screenshot of the display 900 in which a large divergence of visual resources 956 is represented. FIG. 9C further shows an area of maximal salience 962 at a time 938. In some embodiments, the display 900 may include a view looking through the area of maximal salience 962 (e.g., through the funnel) at a particular time 938 or over time. For example, the display may be a dynamic display including a "fly through" display through the funnel 950 wherein the area of maximal salience may be viewed continuously over time as shown in FIG. 9D.

The displays (e.g., 900) of the present invention may be generated for a sample group of individuals, e.g., to determine a group's distribution of visual resources and/or attention to a particular visual stimulus. The displays according to the present invention may further be used to compare one individual's ocular responses and/or distribution of visual resources with reference to the distribution of visual resources of a control group (e.g., typical responses). The responses and/or distribution of visual resources of two different groups of individuals may also be compared to one another. For example, the present invention may be used to compare the distribution of visual resources of one group of a particular age, IQ, capacity, gender, consumer bracket, ethnicity, or any other demographic characteristic. The present invention may also be used to evaluate and/or diagnose an individual based upon their responses and/or relative scanpath and/or distribution of visual resources to a dynamic or static visual stimulus with reference to an attentional funnel based on a collection of typical responses to the visual stimulus.

Figure 10A:
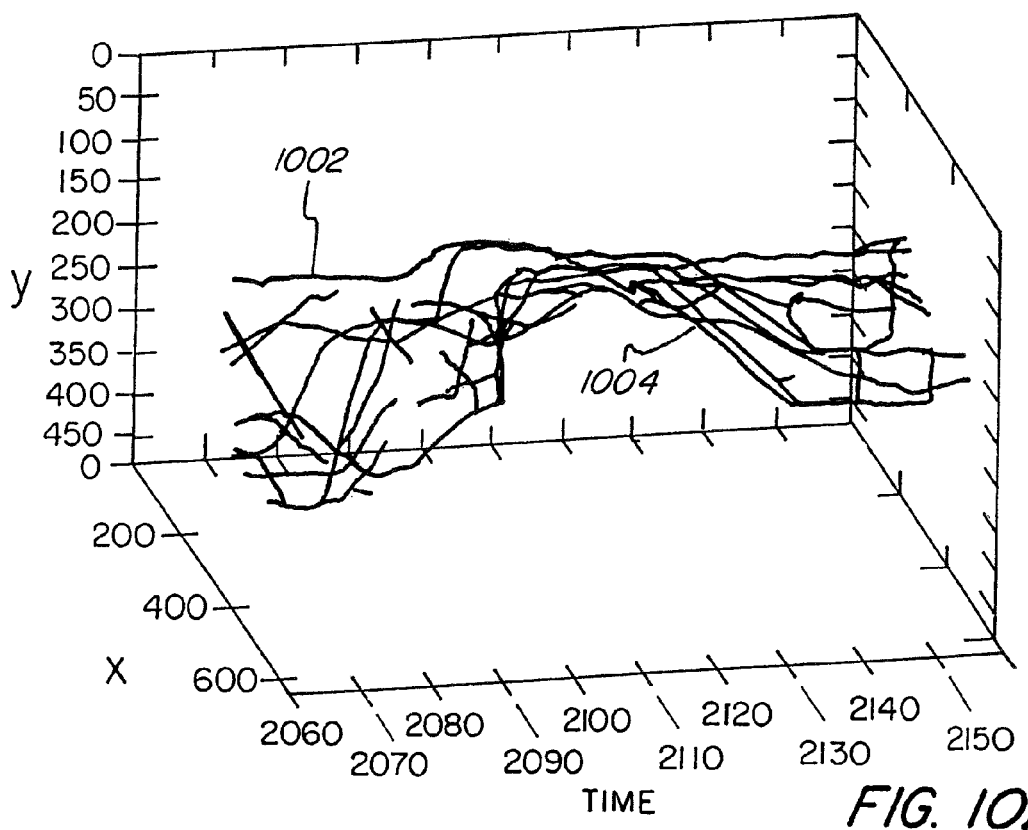
FIGS. 10A-10F show a quantification of statistically significant convergences of visual resources.
Figure 10B:
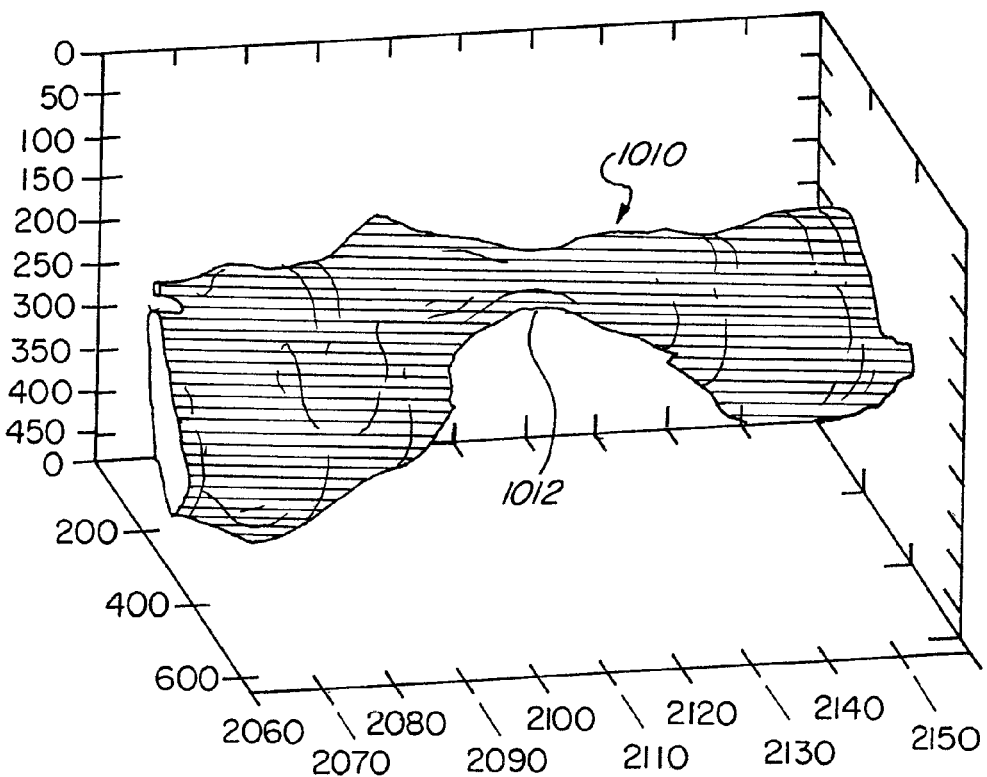
Figure 10C:
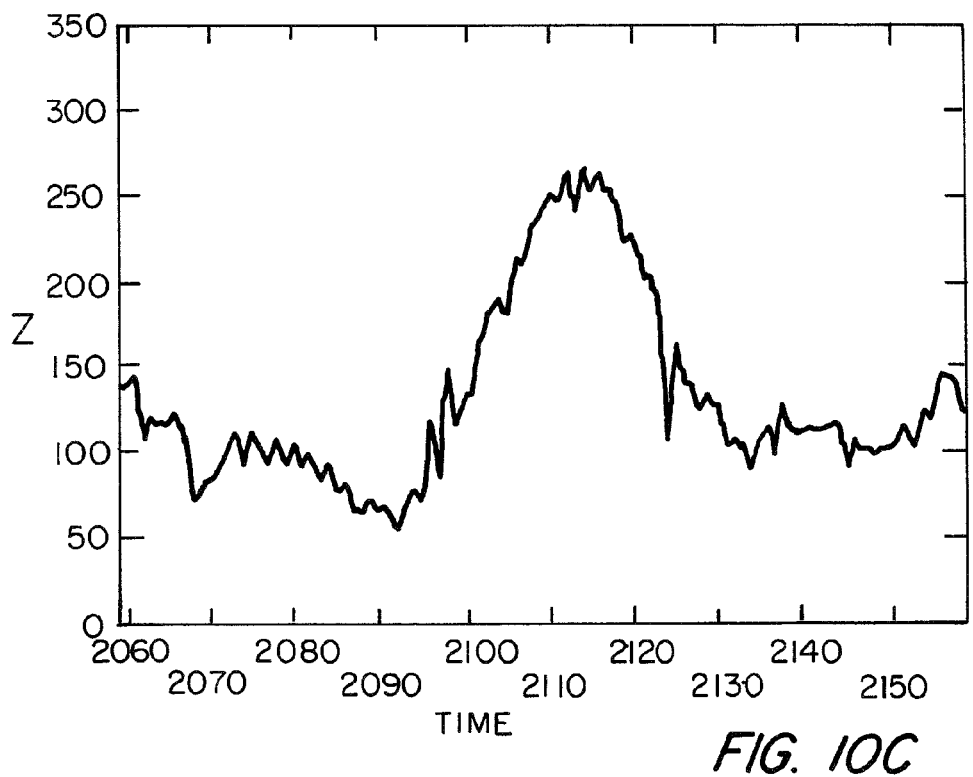

FIGS. 10A-10F shows a means by which to quantify statistically significant convergences in visual scanning. FIG. 10A shows individual scan paths (e.g., 1002, 1004) of ten typically-developing individuals viewing the same visual stimulus. As shown in the scan paths of FIG. 10A, and the corresponding attentional funnel 1010 of FIG. 10B, the group's distribution of visual resources and/or attention may converge at particular times (e.g., 1012). To quantify the significance of the convergence, the average or median value of relative salience may first be determined at each of any number of times (e.g., as described with reference to FIGS. 6B and 7C). FIG. 10C shows the median values of relative salience for the group of viewers plotted over time.

Figure 10D:
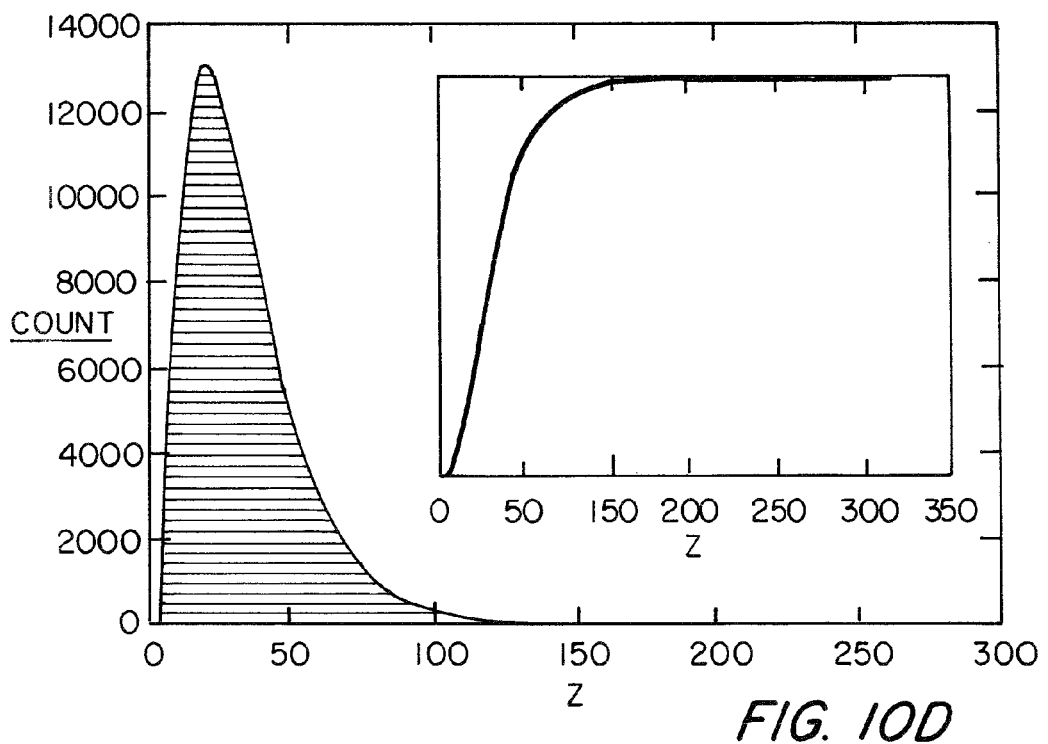
Figure 10E:
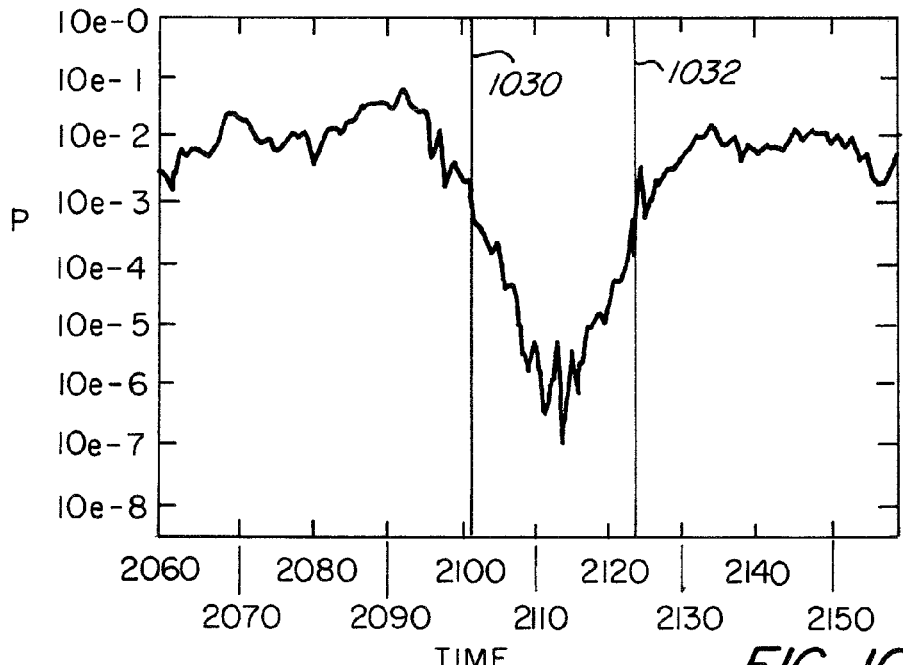
Figure 10F:
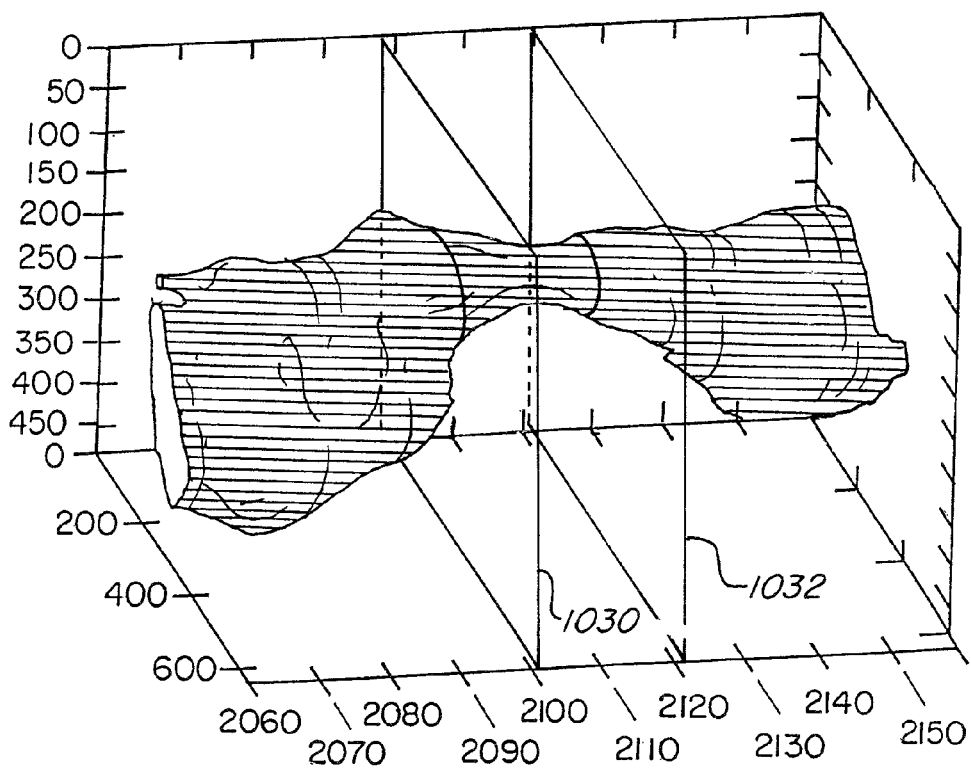

To determine when a convergence of a funnel is statistically significant, the group's median values of relative salience may then be compared to simulated random data (e.g., for 100,000 possible combinations of points of regard for 10 individuals or viewers). For example, a histogram of possible median values or heights of relative salience and an empirical cumulative distribution function for that set of values may be generated from the simulated data as shown in FIG. 10D. A probability of obtaining each median value of relative salience may then be calculated and displayed as shown in FIG. 10E. A probability (p) may then be selected to define when a convergence is statistically significant, i.e., when probability values exceed what could expected by chance. For example, a threshold of p<0.001 may be used. As shown in FIGS. 10E and 10F, this threshold of probability is met between a time 1030 and a time 1032. Therefore, the convergence between time 1030 and 1032 is statistically significant and indicates a location and time of heightened attention.

Figure 11A:
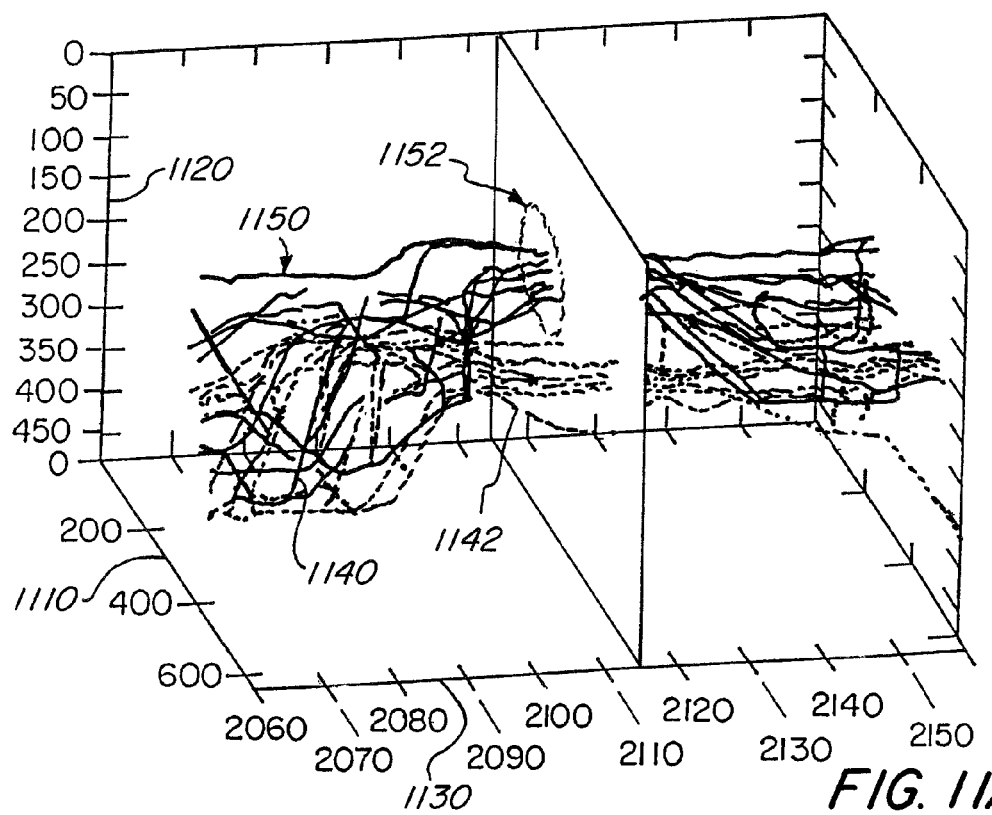
FIGS. 11A-11F show a means by which to compare a group's distribution of visual resources to an individual's ocular responses.
Figure 11B:
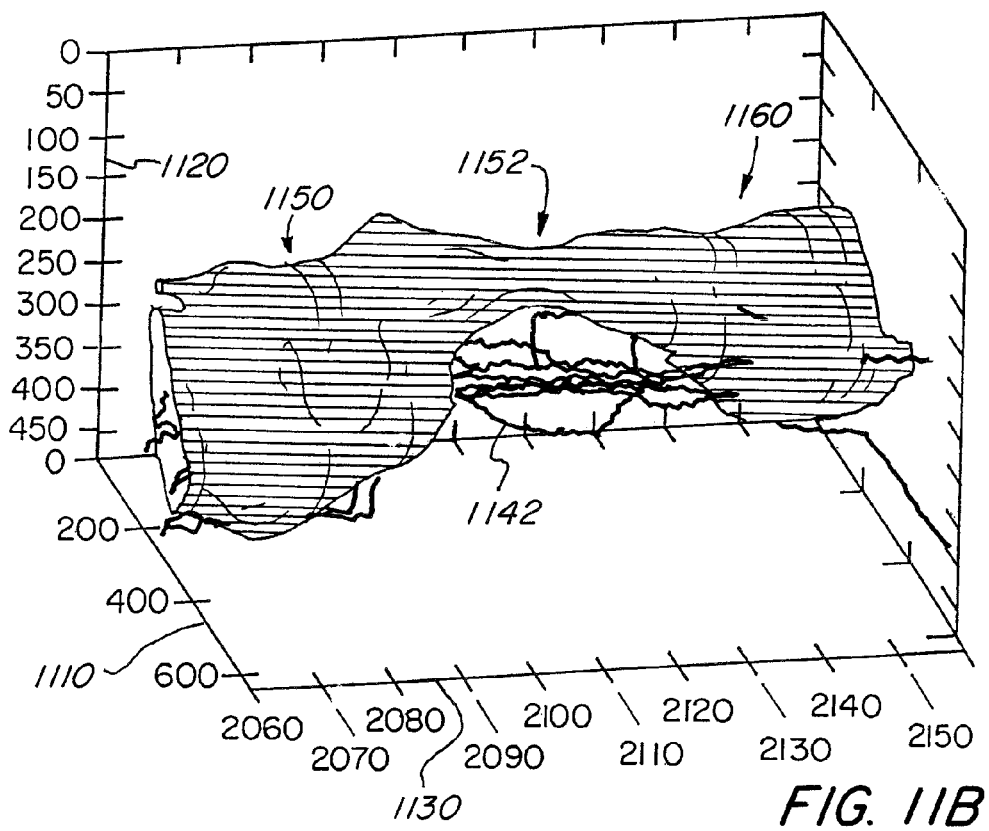

FIGS. 11A-11F show a means by which to compare a group's distribution of visual resources to an individual's ocular responses. FIG. 11A shows a screenshot of a display of several individual's points of regard and/or scan paths (e.g., 1140, 1142) over time. In the present example, the two groups of individuals are represented. A first group (e.g., control group) is indicated by black scan paths (e.g., 1140) and a second group by gray scan paths (e.g., 1142). Shown in FIG. 11B, an attentional funnel 1160 is created from the first group's data. As shown, each group's distribution of visual resources is divergent at a time 1150. However at a time 1152, the first group's distribution of visual resources converges, while the second group does not.

Figure 11C:
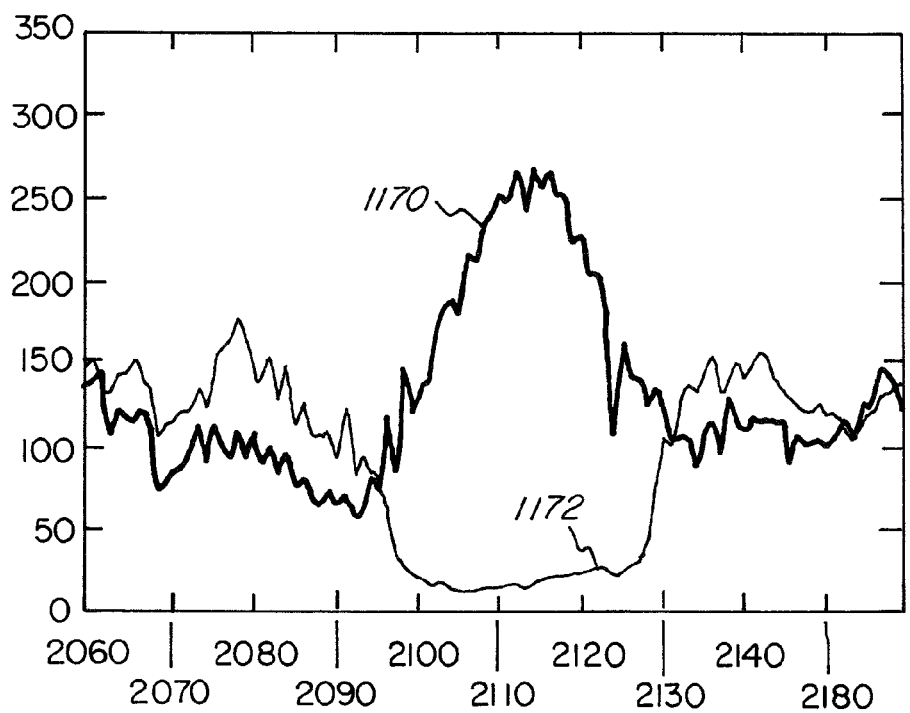
Figure 11D:
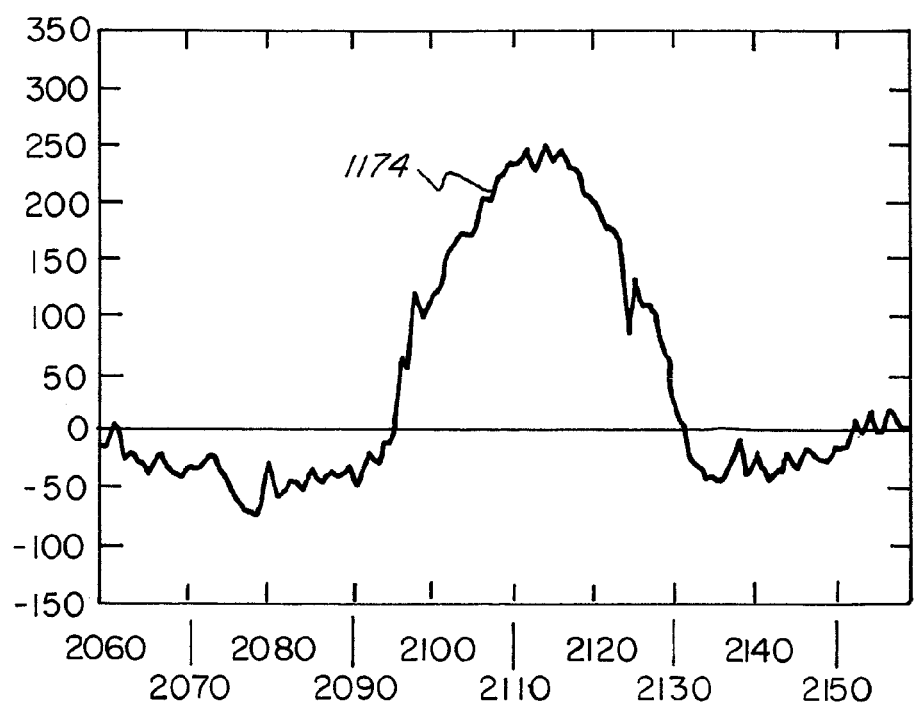
Figure 11E:
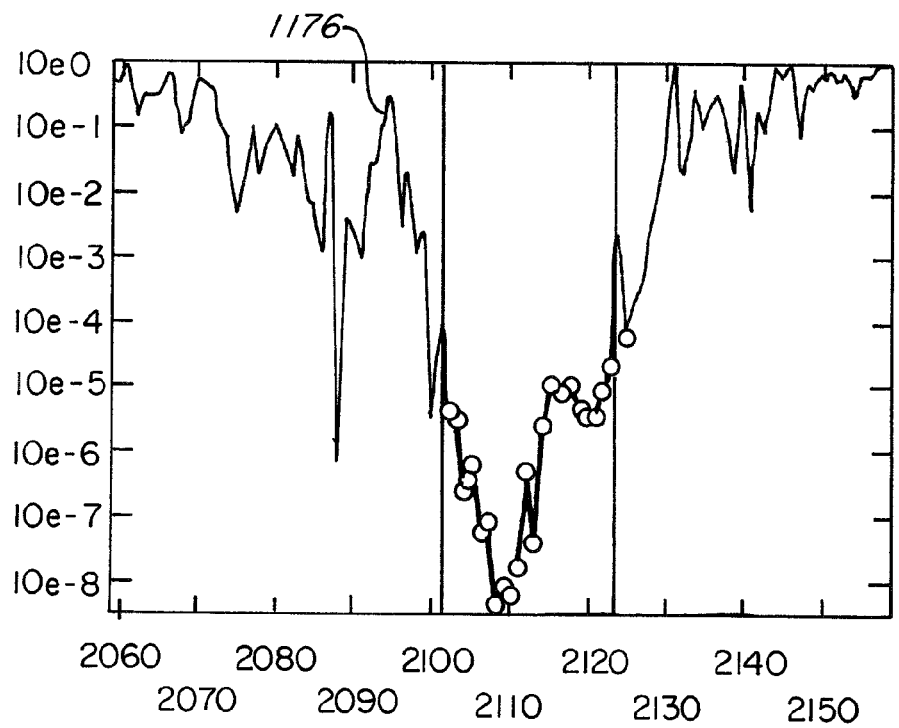

FIG. 11C shows a plot of the median values of relative salience for the first group 1170 compared to those of the second group 1172. In the present example, the first group 1170 represents a group having typical distributions of visual resources for a particular age and IQ level while the second group 1172 represents a group of autistic individuals at the same age and IQ level. The demographics of each group may be known prior to comparison, or in some cases, the present invention may be used to subtype demographics quantitatively. The differences between the first group and the second group may further be illustrated using a difference waveform 1174, shown in FIG. 11D, which depicts the difference between each plot of median values 1170 and 1172 over time. A plot 1176 of the significance of difference as probability (p) values may also be generated as shown in FIG. 11E. In some embodiments, the differences are further quantified by comparison of gradient vectors of salience (e.g., for an individual or group) at one or more points in time.

Figure 11F:
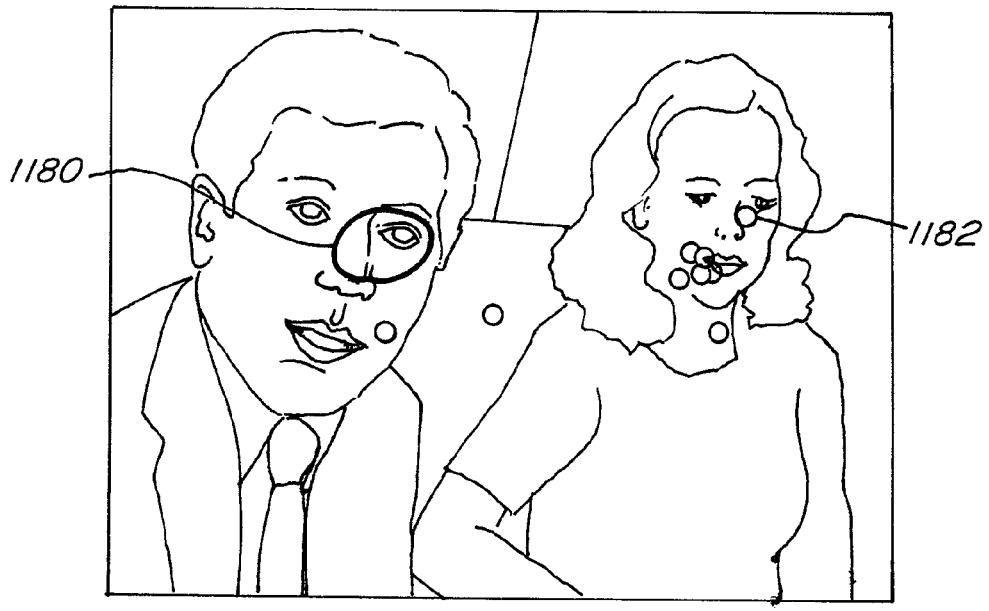

FIG. 11F shows a display including a frame of the visual stimulus corresponding to the time 1152 at which the visual resources of the first group converges. An area of maximal salience 1180 of the first group is shown and indicates an area of heightened attention for the first group. As shown, points of regard (e.g., 1182) of the second group fall outside of the area of maximal salience 1180 of the first group. The sequence illustrated in FIGS. 11A-11F demonstrates an example of the advantageous measure and sensitivity of the system according to the present invention.

Figure 12:
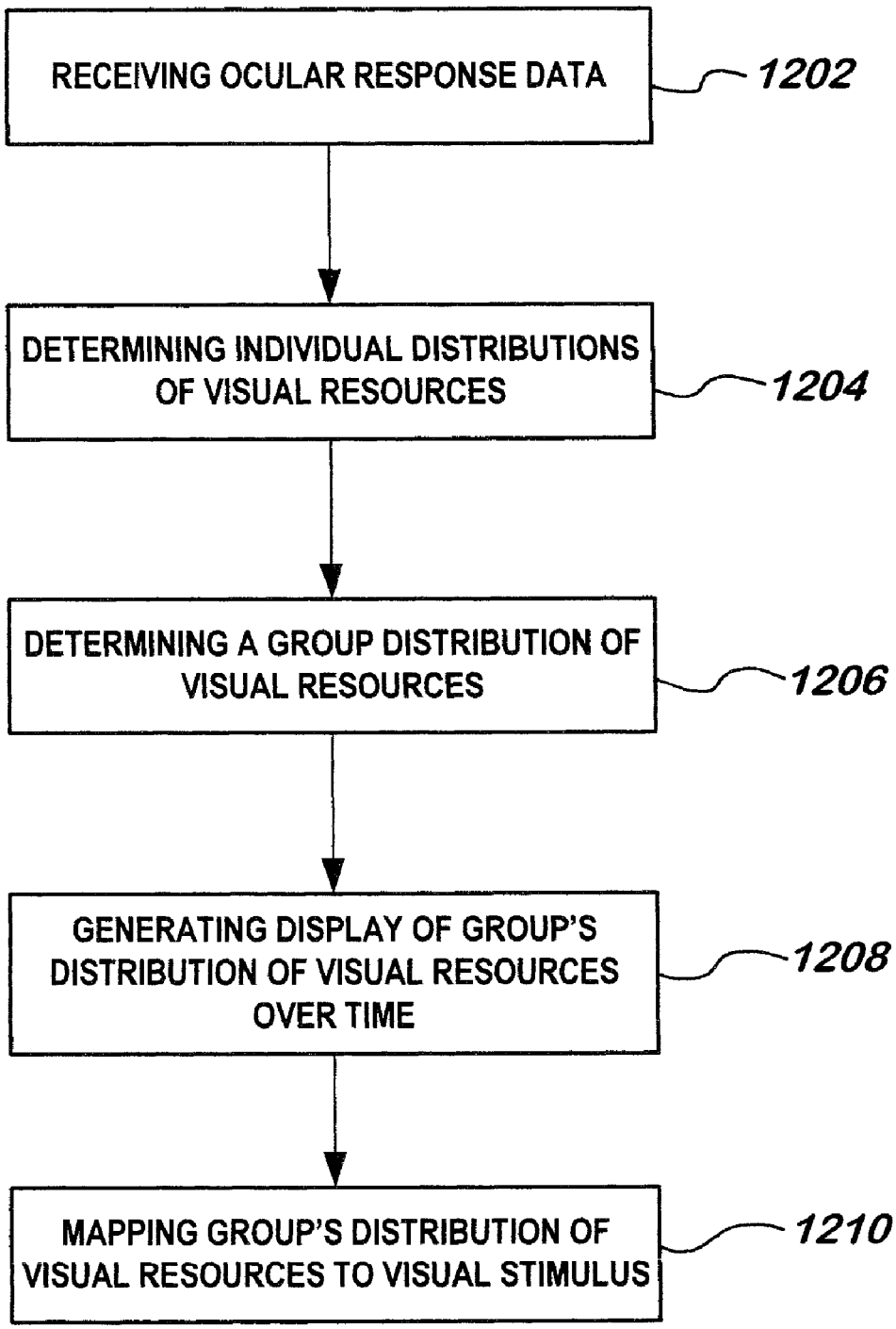
FIG. 12 is a method for quantifying and mapping visual salience employable by the system shown in FIG. 1.

FIG. 12 shows a method of quantifying and mapping visual salience according to the present invention. The method includes a first step 1202 of receiving data indicative of a group of individual's ocular responses to a visual stimulus (e.g., static or dynamic). The data may be received from one or more eye trackers 110. Individual distributions of visual resources may then be determined at each time and for each individual from which data is sampled (step 1204). As described above, determining a distribution of visual resources may include receiving and/or determining a distribution of retinal cells or other indices of biological resources. An average effective distribution of retinal cells may be used for each individual. Alternatively, an effective distribution of retinal cells may be determined or estimated for each individual that is sampled.

In step 1206, a group distribution of visual resources is determined. The group distribution of visual resources may be determined as described above. For example, the individual distributions of visual resources may be summed or otherwise aggregated and an average value of relative salience or attention determined at each time. Areas of maximal salience may be determined to represent the group's distribution of visual resources at each time based on the average value. As described above, convergences or decreased areas of maximal salience provide indication of heightened attention to the corresponding area of the visual stimulus.

In step 1208, a display of the group's distribution of visual resources to the visual stimulus over time is generated. The group's distribution of visual resources and/or areas of maximal salience may then be mapped to the visual stimulus (step 1210). For example, the group distribution determined for each time (e.g., data sample time) may be mapped to a particular frame of a video visual stimulus. For a static visual stimulus, each group distributions may similarly be mapped to the static stimulus (or duplicate representations thereof). The group's areas of maximal salience and/or attention at each time may be connected or extruded over time to create an attentional funnel (e.g., 950). Portions of the visual stimulus may be included in the display to provide a visual presentation of corresponding areas of maximal salience in the visual stimulus over time.

To compare a subject individual to a group, the method may include receiving subject data indicative of a subject's ocular responses to the same dynamic visual stimulus and determining points of regard for the subject. A display of points of regard (e.g., scanpath and/or individual attentional funnel) may be generated and compared to the display of the group's distribution of visual resources to the visual stimulus as described above with reference to FIGS. 11A-11F.

Advantages of the present invention include the provision of a biologically-based means of quantification of viewing patterns to dynamic and static visual stimuli and a means to quantify viewing patterns to visual stimuli in which regions-of-interest over time are determined by the viewers.

Further advantages include the provision of a system and method to determine statistically and behaviorally verifiable quantification of episodes of focused attention for groups of people to particular spatial and temporal locations of both static and dynamic visual stimuli. Further provided is a means to measure relative salience and absolute salience.

The present invention further provides a system and method to quantitatively compare one individual against a group, one group against another group, and to quantitatively using the similarity of individuals to split one large group into smaller groups.

The present invention further provides unique means to visualize and graphically represent ocular response data including, e.g., the oblique presentation of data having an axis of time, continuous representations of salience maps, attentional funnels, and views through attentional funnels. The visualization methods of the present invention provide unique means to visualize and determine statistically significant convergences and episodes of focused visual attention.

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for quantifying and mapping visual salience to a dynamic visual stimulus, comprising:
   a processor;
   software executing on said processor for receiving data indicative of a group of individual's ocular responses while viewing a dynamic visual stimulus, the dynamic visual stimulus changing over time;
   software executing on said processor for generating a distribution of visual resources for each individual in the group at each of a plurality of times during the viewing of the dynamic visual stimulus, said distribution of visual resources for each individual representing an allocation of each of at least two portions of the individual's visual resources across each of at least two portions of the dynamic visual stimulus viewed by the particular individual at the particular time;
   software executing on said processor for generating a distribution of the group's visual resources at each of the plurality of times during the viewing of the dynamic visual stimulus by aggregating the distributions of each of the individuals at each of the plurality of times; and
   software executing on said processor for generating a graphical display of the distribution of the group's visual resources on the dynamic visual stimulus over time, the graphical display illustrating the allocation of each portion of the group's visual resources across each portion of the dynamic visual stimulus viewed by the group at each of the plurality of times throughout the viewing of the dynamic visual stimulus, wherein the graphical display includes at least a portion of the dynamic visual stimulus.

2. The system according to claim 1, wherein said software for generating the distribution of visual resources generates each distribution based on the both the received data and an actual or mathematical approximation of a distribution of biological visual resources.

3. The system according to claim 1, wherein the graphical display of the group distribution of the group's visual resources includes a display of an area of maximal salience on the dynamic visual stimulus at each of the different times.

4. The system according to claim 3, wherein the graphical display includes a three-dimensional extrusion of the areas of maximal salience over a time period including each of the plurality of times.

5. The system according to claim 4, wherein a decrease in area of maximal salience represents a heightened attention to the corresponding area of the visual stimulus.

6. The system according to claim 3, wherein the graphical display includes a three-dimensional attentional funnel comprising each of the areas of maximal salience.

7. The system according to claim 3, wherein the area of maximal salience at each of the plurality of times is based on an average of the group distribution of visual resources at each of the plurality of times.

8. The system according to claim 1, wherein the graphical display of the distribution of the group's visual resources is a continuous graphical display changing over time.

9. The system according to claim 1, wherein the dynamic visual stimulus is video imagery, wherein each of the plurality of times corresponds to a different frame of the video imagery.

10. The system according to claim 1, wherein the dynamic visual stimulus is a live event.

11. The system according to claim 1, further comprising:
    software executing on said processor for receiving stimulus data, wherein the graphical display of the distribution of the group's visual resources includes at least a portion of the stimulus data.

12. A system for quantifying and mapping visual salience to a dynamic visual stimulus, comprising:
    a dynamic visual stimulus, the dynamic visual stimulus changing over time;
    a processor;
    software executing on said processor for receiving data indicative of at least one individual's ocular response while viewing the dynamic visual stimulus;
    software executing on said processor for determining at least one point of regard of the individual at each of a plurality of times based on the data;
    software executing on said processor for generating a graphical display of the at least one individual's points of regard to the dynamic visual stimulus over time;
    software executing on said processor for comparing the at least one individual's points of regard to the dynamic visual stimulus over time to a distribution of a group's visual resources to the dynamic visual stimulus over time; and
    wherein the graphical display includes a representation of the individual's points of regard to the dynamic visual stimulus over time and a representation of an allocation of each of at least two portions of the group's visual resources across each of at least two portions of the dynamic visual stimulus viewed by the group at each of the plurality of times throughout the viewing of the dynamic visual stimulus, wherein the display includes at least a portion of the dynamic visual stimulus.

13. The system according to claim 12, further comprising:
    a device for tracking movement of at least one eye of the at least one individual.

14. The system according to claim 12,
wherein said software for receiving data receives data indicative of at least two individual's ocular response to the dynamic visual stimulus,
wherein said software for determining at least one point of regard determines at least one point of regard for each of the at least two individuals.

15. The system according to claim 14,
wherein the display includes each of the at least two individual's points of regard over the plurality of times.

16. A system for quantifying and mapping visual salience to a static visual stimulus, comprising:
a processor;
software executing on said processor for receiving data indicative of a group of individual's ocular responses while viewing a static visual stimulus over a period of time;
software executing on said processor for generating a distribution of visual resources for each individual in the group at each of a plurality of times during the viewing of the static visual stimulus, said distribution of visual resources for each individual representing an allocation of each of at least two portions of the individual's visual resources across each of at least two portions of the static visual stimulus viewed by the particular individual at the particular time;
software executing on said processor for generating a distribution of the group's visual resources at each of the plurality of times during the viewing of the static visual stimulus by aggregating the distributions of each of the individuals at each of the plurality of times; and
software executing on said processor for generating a three-dimensional graphical display of the group distribution of the group's visual resources on the static visual stimulus over the period of time, the graphical display illustrating the allocation of each portion of the group's visual resources across each portion of the static visual stimulus viewed by the group at each of the plurality of times throughout the viewing of the static visual stimulus, wherein the graphical display includes at least a portion of the static visual stimulus.

17. The system according to claim 16, wherein the graphical display of the group distribution of the group's visual resources includes an area of maximal salience at each of the plurality of times, each area of maximal salience corresponding to an area of the static visual stimulus.

18. The system according to claim 17, wherein the graphical display includes a three-dimensional attentional funnel comprising the areas of maximal salience.

19. The system according to claim 18, wherein a convergence of the attentional funnel at a particular time represents a heightened attention to the corresponding area of the static visual stimulus at the particular time.

20. A method for quantifying and mapping visual salience to a visual stimulus, comprising the steps of:
receiving data indicative of a group of individual's ocular responses while viewing a dynamic visual stimulus, the dynamic visual stimulus changing over time;
generating a first distribution of visual resources for each individual in the group at a first time during the viewing of the dynamic visual stimulus, said distribution representing an allocation of each portion of the individual's visual resources across each portion of the dynamic visual stimulus viewed by the particular individual at the first time;
generating a second distribution of visual resources for each individual in the group at each of at least one additional time during the viewing of the dynamic visual stimulus, said distribution representing the allocation of each portion of the individual's visual resources across each portion of the dynamic visual stimulus viewed by the particular individual at each of the at least one additional times;
generating data indicative of a group distribution of the group's visual resources at each of the at least two times by aggregating the data indicative of the first and second non-uniform distributions of each of the at least a portion of the individuals; and
generating a graphical display of the distribution of the group's visual resources on the dynamic visual stimulus over time, the graphical display illustrating the allocation of each portion of the group's visual resources across each portion of the dynamic visual stimulus viewed by the group throughout the viewing of the dynamic visual stimulus.

21. The method according to claim 20, wherein said step of generating the graphical display includes mapping the distribution of the group's visual resources to the visual stimulus.

22. The method according to claim 21, wherein the visual stimulus is a video, wherein the mapping includes mapping each of the first and additional times to a particular frame of the video.

23. The method according to claim 20, wherein said step of generating the data indicative of the distribution of the group's visual resources includes calculating an average value of relative salience at each of the first and additional times.

24. The method according to claim 23, wherein said step of generating the data indicative of the distribution of the group's visual resources includes determining an area of maximal salience at each of the first and additional times based on the average value.

25. The method according to claim 24, wherein the graphical display includes the areas of maximal salience extruded over each of the first and additional times.

26. The method according to claim 24, wherein the graphical display includes a three-dimensional attentional funnel comprising the areas of maximal salience.

27. The method according to claim 20, wherein the received data includes at least two ocular responses per second for each of at least a portion of the individuals of the group.

28. The method according to claim 20, wherein said step of generating a distribution of visual resources including determining a distribution of retinal cells.

29. The method according to claim 20, further comprising the steps of:
receiving subject data indicative of at least one subject's ocular responses to the visual stimulus;
determining at least one point of regard at each of the first and additional times for each of the at least one subjects based on the subject data, and
generating a graphical display of the at least one subject's points of regard over time.

30. The method according to claim 29, further comprising the step of:
comparing the graphical display of the at least one subject's points of regard to the graphical display of the distribution of the group's visual resources to the visual stimulus.

31. The method according to claim 30, wherein said step of comparing includes comparing values of relative salience of the group over time to the display of the at least one subject's points of regard over time.

32. The system according to claim 1, wherein the distribution of visual resources for each individual is a non-uniform distribution.

33. The system according to claim 16, wherein the distribution of visual resources for each individual is a non-uniform distribution.

34. The method according to claim 20, wherein each of the first and second distributions of visual resources are non-uniform distributions.

* * * * *